(12) United States Patent  
Nagata

(10) Patent No.: US 10,975,041 B2  
(45) Date of Patent: Apr. 13, 2021

(54) METHOD FOR PRODUCING 5,5-DISUBSTITUTED-4,5-DIHYDROISOXAZOLE

(71) Applicant: KUMIAI CHEMICAL INDUSTRY CO., LTD., Tokyo (JP)

(72) Inventor: Toshihiro Nagata, Tokyo (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 16/954,082

(22) PCT Filed: Dec. 13, 2018

(86) PCT No.: PCT/JP2018/045921  
§ 371 (c)(1),  
(2) Date: Jun. 15, 2020

(87) PCT Pub. No.: WO2019/117255  
PCT Pub. Date: Jun. 20, 2019

(65) Prior Publication Data  
US 2021/0047280 A1 Feb. 18, 2021

(30) Foreign Application Priority Data  
Dec. 15, 2017 (JP) .............................. JP2017-240521

(51) Int. Cl.  
*C07D 261/04* (2006.01)  
*B01J 31/04* (2006.01)  
*B01J 31/02* (2006.01)

(52) U.S. Cl.  
CPC ........ *C07D 261/04* (2013.01); *B01J 31/0231* (2013.01); *B01J 31/04* (2013.01)

(58) Field of Classification Search  
CPC ................................................. C07D 261/04  
See application file for complete search history.

(56) References Cited

U.S. PATENT DOCUMENTS

| 5,696,271 A | 12/1997 | Takada et al. |
| 2004/0110749 A1 | 6/2004 | Nakatani et al. |
| 2012/0238760 A1 | 9/2012 | Frassetto |

FOREIGN PATENT DOCUMENTS

| JP | 2013-512202 A | 4/2013 |
| JP | 2016-132643 A | 7/2016 |
| JP | 6737966 B2 | 7/2020 |
| WO | 95/22533 A1 | 8/1995 |
| WO | 02/062770 A1 | 8/2002 |

OTHER PUBLICATIONS

Lozynski, Marek et al., "Two Phase Preparation of Oximes" Polish Journal of Chemistry, 1986, 60(4-6), p. 625-629; Cited in JP Office Action dated Jan. 23, 2020. (5 pages).  
Notification of Reasons for Refusal dated Jan. 23, 2020, issued in counterpart Japanese Application No. 2019-559204, with English translation. (8 pages).  
Decision to Grant a Patent dated Jul. 1, 2020, issued in counterpart Japanese Application No. 2019-559204, with English translation. (7 pages).  
Written Opinion dated May 29, 2020, issued in counterpart Japanese Application No. 2019-559204, with English translation. (19 pages).  
Written Amendment dated May 29, 2020, issued in counterpart Japanese Application No. 2019-559204, with English translation. (7 pages).  
International Search Report dated Feb. 26, 2019, issued in counterpart International Application No. PCT/JP2018/045921. (3 page).  
Isager et al., "Reactions with a,B-Unsaturated Nitrile Oxides, Synthetic Studies in the terpene Field. Synthesis of Tagetones, Ocimenones, Deodarone and Atlantone", Acta Chemica Scandinavica, (1990), vol. 44, No. 8, pp. 806-813. Cited in ISR. (8 pages).  
Pohjakallio et al., "A Versatile Entry to 3-Unsubstituted 2-Isoxazoline", SYNLETT (2008), No. 6, pp. 0827-0830. Cited in Specification. (4 pages).  
Hansen et al., "Halogenation of Vinyl Ketoximes. Synthese of Isoxazoles and Preparation and Silver Ion-Promoted Reactions of 4-Halo-2-isoxazolines", Journal of Heterocyclic Chemistry, (1980), vol. 17, No. 3, pp. 475-479. Cited in ISR. (5 pages).  
Pohjakallio et al., "Synthesis of 2-Isoxazolines: Enantioselective and Racemic Methods Based on Conjugate Addistions of Oximes", Chem. Eur. J., (2010), vol. 16, pp. 11325-11339. Cited in Specification. (15 pages).  
Li et al., "Cobalt-catalyzed aerobic oxidative cyclization of B,Y-unsaturated oximes", Tetrahedron, (2013), vol. 69, No. 15, pp. 3274-3280. Cited in ISR. (7 pages).

(Continued)

*Primary Examiner* — Kamal A Saeed  
(74) *Attorney, Agent, or Firm* — Westerman, Hattori, Daniels & Adrian, LLP

(57) ABSTRACT

The present invention addresses the problem of providing an industrially preferable, economical, and environmentally friendly method for producing the 4,5-dihydroisoxazole represented by a formula (3).

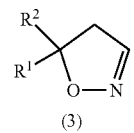

(3)

The present invention enables the compound of a formula (3) to be produced by reacting the compound of a formula (2) according to the reaction represented by a reaction formula in the presence of an acid catalyst.

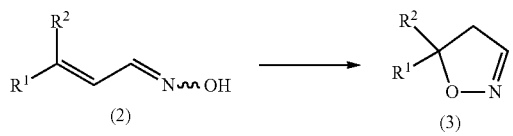

20 Claims, No Drawings

(56) References Cited

OTHER PUBLICATIONS

Yamamoto et al., "Manganese-Promoted Oxidative Cyclization of Unsaturated Oximes Using Molecular Oxygen in Air under Ambient Conditions", European Journal of Organic Chemistry, (2016), vol. 2016, No. 31, pp. 5216-5219. Cited in ISR. (4 pages).

Mahadevan et al., "Synthesis of novel naphtho[2,1-b]furo pyrazolyl, isoxazolyl and pyridyl derivatives as potential antimicrobial agents", Indian Journal of Chemistry, Section B: Organic Chemistry Including Medicinal Chemistry, (2005), vol. 44B, No. 4, pp. 789-793. Cited in ISR. (5 pages).

Matoba et al., "Enantioselective Synthesis of Trifluoromethyl-Substituted 2-Isoxazolines: Asymmetric Hydroxylamine/Enone Cascade Reaction", Angewandte Chemie, International Edition, (2010), vol. 49, No. 33, pp. 5762-5766. Cited in ISR. (5 pages).

METHOD FOR PRODUCING 5,5-DISUBSTITUTED-4,5-DIHYDROISOXAZOLE

TECHNICAL FIELD

The present invention relates to a process for producing a compound of a formula (3):

[Chemical Formula 1]

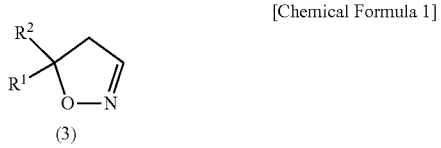

(3)

wherein, $R^1$ and $R^2$ are as described later, i.e., a 5,5-disubstituted-4,5-dihydroisoxazole. Herein, the compound of the formula (3) is also referred to as a 5,5-disubstituted-2-isoxazoline.

BACKGROUND ART 5,5-Disubstituted-4,5-dihydroisoxazoles of the formula (3) are useful as intermediates for the production of pharmaceuticals, agricultural chemicals, etc. WO 2002/062770 (Patent Document 1) discloses useful herbicides. Among them, pyroxasulfone is well known as a herbicide having excellent herbicidal activity. Furthermore, JP 2013-512202 A (Patent Document 2) discloses that the 5,5-disubstituted-4,5-dihydroisoxazoles of the formula (3) are important intermediates for the herbicides described in Patent Document 1.

JP 2013-512202 A (Patent Document 2) discloses a process for producing 5,5-disubstituted-4,5-dihydroisoxazoles.

Scheme 2 of Patent Document 2:

[Chemical Formula 2]

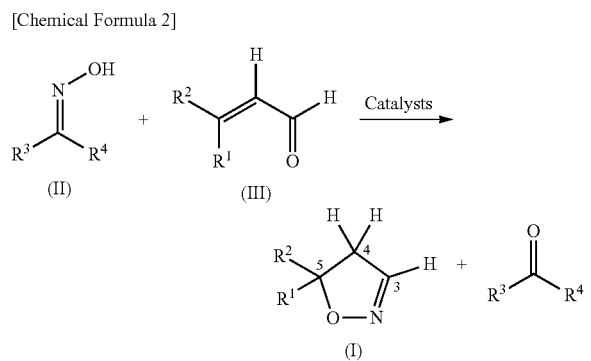

As shown in the above scheme, in the process described in Patent Document 2, an oxime of the formula (II) is reacted with a carbonyl compound of the formula (III) (a β-disubstituted-α,β-unsaturated aldehyde) in the presence of an acid catalyst or an acid-base catalyst, to obtain a 5,5-disubstituted-4,5-dihydroisoxazole of the formula (I).

In the process described in Patent Document 2, the oxime of the formula (II) to be used as a raw material is a ketone oxime. As a result, a ketone ($R^3C(=O)R^4$) is produced as a by-product (see the above scheme). In fact, in the examples disclosed in Patent Document 2, acetone oxime was used and acetone was produced as a by-product (see Examples of Patent Document 2). The ketone as a by-product will be a waste that places a burden on the environment. Therefore, this process has the problem of placing a burden on the environment.

In addition, since the ketone is produced as a by-product, this process causes a decrease in atom efficiency. Therefore, the productivity of the target 5,5-disubstituted-4,5-dihydroisoxazole decreases. Furthermore, because a step of separating the ketone as a by-product and/or the disposal of the ketone as a waste are required, operability and/or economic efficiency decreases. Therefore, this process is not economical and is not industrially preferable.

Synlett 2008, No. 6, 827-830 (Non-Patent Document 1) and Chem. Eur. J. 2010, Vol. 16, 11325-11339 (Non-Patent Document 2) describe processes of producing a 4,5-dihydroisoxazole derivative by using a ketone oxime. Because of the use of the ketone oxime as the raw material oxime, the processes described in Non-Patent Documents 1 and 2 have the same problems as those of the process described in JP 2013-512202 A (Patent Document 2). That is, the processes described in Non-Patent Documents 1 and 2 also have poor productivity and poor operability, and place a heavy burden on the environment, and are not economical, and are not industrially preferable.

CITATION LIST

Patent Document

Patent Document 1: WO 2002/062770 A1
Patent Document 2: JP 2013-512202 A

Non-Patent Document

Non-Patent Document 1: Synlett 2008, No. 6, 827-830
Non-Patent Document 2: Chem. Eur. J. 2010, Vol. 16, 11325-11339

SUMMARY OF INVENTION

Technical Problem

There has been desired an industrially preferable process for producing a compound of the above formula (3), i.e., the target 5,5-disubstituted-4,5-dihydroisoxazole, the process being capable of solving the above-described one or more disadvantages or problems in the prior art. Therefore, an object of the present invention is to provide a process for producing the target compound, which process is industrially preferable, economical, and environmentally friendly. A more specific object of the present invention is to provide a process that can suppress the production of a by-product and/or a waste and can improve atom efficiency.

Another more specific object of the present invention is to provide a process that can produce a target compound efficiently by a simple operation even if an inexpensive catalyst is used.

Solution to Problem

In view of the circumstances as described above, the present inventor has earnestly studied a process for producing a compound of the formula (3). As a result, the present inventor unexpectedly found that the above problems can be solved by providing the following processes for producing the compound of the formula (3). The present inventor has accomplished the present invention based on this finding.

That is, in one embodiment, the present invention is as follows.

[I-1] A process for producing a compound of the formula (3):

[Chemical Formula 3]

(3)

wherein $R^1$ and $R^2$ are each independently an optionally substituted (C1-C6)alkyl; an optionally substituted (C3-C6) cycloalkyl; an optionally substituted (C2-C6)alkenyl; an optionally substituted (C2-C6)alkynyl; an optionally substituted (C1-C6)alkoxy; or an optionally substituted phenyl; or $R^1$ and $R^2$, together with the carbon atom to which they are attached form a 4- to 12-membered carbocyclic ring, wherein the formed ring is optionally substituted, which comprises the following step:

step (B): reacting a compound of the formula (2) in the presence of an acid catalyst to produce the compound of the formula (3),

[Chemical Formula 4]

(2) → (3)

wherein $R^1$ and $R^2$ are as defined above.

[I-2] The process according to [I-1], wherein the compound of the formula (2) is produced by a process comprising the following step (A), step (A): reacting a compound of the formula (1) with an oximating agent to produce the compound of the formula (2),

[Chemical Formula 5]

(1) → (2)

wherein $R^1$ and $R^2$ are as defined above.

[I-3] A process for producing a compound of the formula (3):

[Chemical Formula 100]

(3)

wherein $R^1$ and $R^2$ are as defined above, which comprises the following step:

step (A): reacting a compound of the formula (1) with an oximating agent to produce a compound of the formula (2),

[Chemical Formula 100]

(1) → (2)

wherein $R^1$ and $R^2$ are as defined above, step (B): reacting the compound of the formula (2) in the presence of an acid catalyst to produce the compound of the formula (3),

[Chemical Formula 100]

(2) → (3)

wherein $R^1$ and $R^2$ are as defined above.

[I-4] The process according to [I-2] or [I-3], wherein the oximating agent in the step (A) is hydroxylamine or a salt thereof.

[I-5] The process according to [I-2] or [I-3], wherein the oximating agent in the step (A) is hydroxylamine, hydroxylamine hydrochloride or hydroxylamine sulfate.

[I-6] The process according to [I-2] or [I-3], wherein the oximating agent in the step (A) is a 45% to 50% hydroxylamine aqueous solution, hydroxylamine hydrochloride or hydroxylamine sulfate.

[I-7] The process according to [I-2] or [I-3], wherein the oximating agent in the step (A) is hydroxylamine hydrochloride or hydroxylamine sulfate.

[I-8] The process according to [I-2] or [I-3], wherein the oximating agent in the step (A) is hydroxylamine hydrochloride.

[I-9] The process according to [I-2] or [I-3], wherein the oximating agent in the step (A) is hydroxylamine sulfate.

[I-10] The process according to any one of [I-2] to [I-9], wherein the reaction of the step (A) is performed in the presence of a base.

[I-11] The process according to [I-10], wherein the base in the step (A) is sodium hydroxide, potassium hydroxide, sodium carbonate, potassium carbonate, sodium hydrogen carbonate, potassium hydrogen carbonate or ammonia.

[I-12] The process according to [I-10], wherein the base in the step (A) is sodium hydroxide or ammonia.

[I-13] The process according to any one of [I-2] to [I-12], wherein the reaction of the step (A) is performed in the presence of one or more (preferably one or two, more preferably one) solvent(s) selected from acetonitrile, toluene, xylene, chlorobenzene, dichlorobenzene and dichloromethane, and a water solvent.

[I-14] The process according to any one of [I-2] to [I-12], wherein the reaction of the step (A) is performed in the presence of one or more (preferably one or two, more preferably one) solvent(s) selected from toluene, xylene, chlorobenzene, dichlorobenzene and dichloromethane, and a water solvent.

[I-15] The process according to [I-2] to [I-12], wherein the reaction of the step (A) is performed in the presence of one or more (preferably one or two, more preferably one) solvent(s) selected from acetonitrile and dichloromethane, and a water solvent.

[I-16] The process according to any one of [I-2] to [I-12], wherein the reaction of the step (A) is performed in the presence of a solvent composed of a combination of water and dichlorobenzene (i.e., a mixed solvent of water and dichlorobenzene).

[I-17] The process according to any one of [I-2] to [I-16], wherein the reaction of the step (A) is performed at 0° C. to 80° C.

[I-18] The process according to any one of [I-2] to [I-16], wherein the reaction of the step (A) is performed at 10° C. to 50° C.

[I-19] The process according to any one of [I-1] to [I-18], wherein the acid catalyst in the step (B) is one or more (preferably one to three, more preferably one or two, even more preferably one) acid catalyst(s) selected from the group consisting of mineral acids, carboxylic acids, sulfonic acids, phosphoric acids and Lewis acids.

[I-20] The process according to any one of [I-1] to [I-18], wherein the acid catalyst in the step (B) is one or more (preferably one to three, more preferably one or two, even more preferably one) acid catalyst(s) selected from the group consisting of hydrochloric acid, sulfuric acid, nitric acid, trifluoroacetic acid, trichloroacetic acid, dichloroacetic acid, maleic acid, maleic anhydride, methanesulfonic acid, trifluoromethanesulfonic acid, benzenesulfonic acid, p-toluenesulfonic acid, 10-camphorsulfonic acid, phosphoric acid, ethyl phosphate, phenyl phosphate, diethyl phosphate, diphenyl phosphate, transition metal triflate, and iodine.

[I-21] The process according to any one of [I-1] to [I-18], wherein the acid catalyst in the step (B) is one or more (preferably one to three, more preferably one or two, even more preferably one) acid catalyst(s) selected from the group consisting of hydrochloric acid, sulfuric acid, nitric acid, trifluoroacetic acid, trichloroacetic acid, dichloroacetic acid, maleic acid, maleic anhydride, methanesulfonic acid, trifluoromethanesulfonic acid, benzenesulfonic acid, p-toluenesulfonic acid, 10-camphorsulfonic acid, diphenyl phosphate, copper(II) triflate, silver(I) triflate, and iodine.

[I-22] The process according to any one of [I-1] to [I-18], wherein the acid catalyst in the step (B) is one or more (preferably one to three, more preferably one or two, even more preferably one) acid catalyst(s) selected from the group consisting of nitric acid, trifluoroacetic acid, trichloroacetic acid, dichloroacetic acid, maleic acid, maleic anhydride, methanesulfonic acid, trifluoromethanesulfonic acid, benzenesulfonic acid, p-toluenesulfonic acid, 10-camphorsulfonic acid, and diphenyl phosphate.

[I-23] The process according to any one of [I-1] to [I-18], wherein the acid catalyst in the step (B) is one or more (preferably one to three, more preferably one or two, even more preferably one) acid catalyst(s) selected from the group consisting of nitric acid, trifluoroacetic acid, trichloroacetic acid, dichloroacetic acid, maleic acid, maleic anhydride, methanesulfonic acid, benzenesulfonic acid, p-toluenesulfonic acid, and diphenyl phosphate.

[I-24] The process according to any one of [I-1] to [I-18], wherein the acid catalyst in the step (B) is one or more (preferably one to three, more preferably one or two, even more preferably one) acid catalyst(s) selected from the group consisting of nitric acid, trifluoroacetic acid, trichloroacetic acid, maleic acid, maleic anhydride, benzenesulfonic acid, p-toluenesulfonic acid, and diphenyl phosphate.

[I-25] The process according to any one of [I-1] to [I-18], wherein the acid catalyst in the step (B) is one or more (preferably one to three, more preferably one or two, even more preferably one) acid catalyst(s) selected from the group consisting of nitric acid, trifluoroacetic acid, trichloroacetic acid, maleic acid, maleic anhydride, p-toluenesulfonic acid, and diphenyl phosphate.

[I-26] The process according to any one of [I-1] to [I-18], wherein the acid catalyst in the step (B) is one or more (preferably one to three, more preferably one or two, even more preferably one) acid catalyst(s) selected from the group consisting of nitric acid, trifluoroacetic acid, trichloroacetic acid, maleic acid, maleic anhydride, benzenesulfonic acid, and p-toluenesulfonic acid.

[I-27] The process according to any one of [I-1] to [I-18], wherein the acid catalyst in the step (B) is one or more (preferably one to three, more preferably one or two, even more preferably one) acid catalyst(s) selected from the group consisting of nitric acid, trifluoroacetic acid, trichloroacetic acid, maleic acid, maleic anhydride, and p-toluenesulfonic acid.

[I-28] The process according to any one of [I-1] to [I-18], wherein the acid catalyst in the step (B) is one or more (preferably one to three, more preferably one or two, even more preferably one) acid catalyst(s) selected from the group consisting of nitric acid, trifluoroacetic acid, maleic acid, and p-toluenesulfonic acid.

[I-29] The process according to any one of [I-1] to [I-18], wherein the acid catalyst in the step (B) is trifluoroacetic acid, maleic acid or maleic anhydride.

[I-30] The process according to any one of [I-1] to [I-18], wherein the acid catalyst in the step (B) is trifluoroacetic acid or maleic acid.

[I-31] The process according to any one of [I-1] to [I-18], wherein the acid catalyst in the step (B) is trifluoroacetic acid.

[I-32] The process according to any one of [I-1] to [I-18], wherein the acid catalyst in the step (B) is maleic acid or maleic anhydride.

[I-33] The process according to any one of [I-1] to [I-18], wherein the acid catalyst in the step (B) is maleic acid.

[I-34] The process according to any one of [I-1] to [I-33], wherein the reaction of the step (B) is performed in the absence of a base catalyst.

[I-35] The process according to any one of [I-1] to [I-33], wherein the reaction of the step (B) is performed in the presence of a base catalyst.

[I-36] The process according to any one of [I-1] to [I-33], wherein the reaction of the step (B) is performed in the presence of a base catalyst wherein the equivalent amount of the base catalyst is less than the equivalent amount of the acid catalyst.

[I-37] The process according to any one of [I-1] to [I-33], wherein the reaction of the step (B) is performed in the presence of 0.1 to 0.5 equivalents of a base catalyst based on 1 equivalent of the acid catalyst.

[I-38] The process according to any one of [I-1] to [I-33], wherein the reaction of the step (B) is performed in the presence of 0.2 to 0.4 equivalents of a base catalyst based on 1 equivalent of the acid catalyst.

[I-39] The process according to any one of [I-35] to [I-38], wherein the base catalyst in the step (B) is N-methylaniline, morpholine or pyrrolidine.

[I-40] The process according to any one of [I-35] to [I-38], wherein the base catalyst in the step (B) is N-methylaniline.

[I-41] The process according to any one of [I-1] to [I-40], wherein the reaction of the step (B) is performed in the presence of one or more (preferably one or two, more preferably one) solvent(s) selected from acetonitrile, toluene, xylene, chlorobenzene, dichlorobenzene and dichloromethane, and a water solvent.

[I-42] The process according to any one of [I-1] to [I-40], wherein the reaction of the step (B) is performed in the presence of one or more (preferably one or two, more preferably one) solvent(s) selected from toluene, xylene, chlorobenzene, dichlorobenzene and dichloromethane, and a water solvent.

[I-43] The process according to any one of [I-1] to [I-40], wherein the reaction of the step (B) is performed in the presence of one or more (preferably one or two, more preferably one) solvent(s) selected from acetonitrile and dichloromethane, and a water solvent.

[I-44] The process according to any one of [I-1] to [I-40], wherein the reaction of the step (B) is performed in the presence of a solvent composed of a combination of water and dichlorobenzene (i.e., a mixed solvent of water and dichlorobenzene).

[I-45] The process according to any one of [I-1] to [I-40], wherein the reaction of the step (B) is performed in the presence of one or more (preferably one or two, more preferably one) solvent(s) selected from acetonitrile, toluene, xylene, chlorobenzene, dichlorobenzene and dichloromethane.

[I-46] The process according to any one of [I-1] to [I-40], wherein the reaction of the step (B) is performed in the presence of one or more (preferably one or two, more preferably one) solvent(s) selected from toluene, xylene, chlorobenzene, dichlorobenzene and dichloromethane.

[I-47] The process according to any one of [I-1] to [I-40], wherein the reaction of the step (B) is performed in the presence of one or more (preferably one or two, more preferably one) solvent(s) selected from acetonitrile and dichloromethane.

[I-48] The process according to any one of [I-1] to [I-40], wherein the reaction of the step (B) is performed in the presence of a dichlorobenzene solvent.

[I-49] The process according to any one of [I-1] to [I-48], wherein the reaction of the step (B) is performed at 10° C. to 100° C.

[I-50] The process according to any one of [I-1] to [I-48], wherein the reaction of the step (B) is performed at 10° C. to 50° C.

[I-51] The process according to any one of [I-1] to [I-50], wherein $R^1$ and $R^2$ are each independently (C1-C6)alkyl; (C1-C6)haloalkyl; (C3-C6)cycloalkyl; (C2-C6)alkenyl; (C2-C6)alkynyl; (C1-C6)alkoxy; or phenyl optionally substituted with 1 to 5 substituents independently selected from halogen atoms, (C1-C4)alkyl and (C1-C4)haloalkyl; or $R^1$ and $R^2$, together with the carbon atom to which they are attached form a 4- to 6-membered carbocyclic ring.

[I-52] The process according to any one of [I-1] to [I-50], wherein $R^1$ and $R^2$ are each independently (C1-C4)alkyl; (C1-C4)haloalkyl; (C3-C6)cycloalkyl; (C2-C4)alkenyl; (C2-C4)alkynyl; (C1-C4)alkoxy; or phenyl optionally substituted with 1 to 5 substituents independently selected from halogen atoms, (C1-C4)alkyl and (C1-C4)haloalkyl; or $R^1$ and $R^2$, together with the carbon atom to which they are attached form a 4- to 6-membered carbocyclic ring.

[I-53] The process according to any one of [I-1] to [I-50], wherein $R^1$ and $R^2$ are each independently (C1-C4)alkyl or (C1-C4)haloalkyl.

[I-54] The process according to any one of [I-1] to [I-50], wherein $R^1$ and $R^2$ are each independently (C1-C4)alkyl.

[I-55] The process according to any one of [I-1] to [I-50], wherein the compound of the formula (2) is 3-methyl-2-butenal oxime and the compound of the formula (3) is 5,5-dimethyl-4,5-dihydroisoxazole.

[I-56] The process according to any one of [I-2] to [I-50], wherein the compound of the formula (1) is 3-methyl-2-butenal, the compound of the formula (2) is 3-methyl-2-butenal oxime, and the compound of the formula (3) is 5,5-dimethyl-4,5-dihydroisoxazole.

[I-57] The process according to any one of [I-1] to [I-50], wherein $R^1$ and $R^2$ are methyl.

In another embodiment, the invention is as follows.

[II-1] A process for producing a compound of the formula (3):

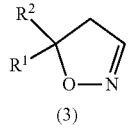

(3)

wherein $R^1$ and $R^2$ are each independently an optionally substituted (C1-C6)alkyl; an optionally substituted (C3-C6)cycloalkyl; an optionally substituted (C2-C6)alkenyl; an optionally substituted (C2-C6)alkynyl; an optionally substituted (C1-C6)alkoxy; or an optionally substituted phenyl; or $R^1$ and $R^2$, together with the carbon atom to which they are attached form a 4- to 12-membered carbocyclic ring, wherein the formed ring is optionally substituted, which comprises the following step:

step (B): reacting a compound of the formula (2) in the presence of an acid catalyst to produce the compound of the formula (3),

[Chemical Formula 4]

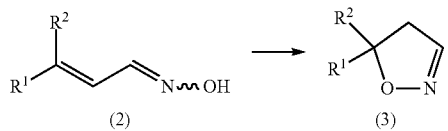

wherein $R^1$ and $R^2$ are as defined above.

[II-2] The process according to [II-1], wherein the compound of the formula (2) is produced by a process comprising the following step (A), step (A): reacting a compound of the formula (1) with an oximating agent to produce the compound of the formula (2),

[Chemical Formula 5]

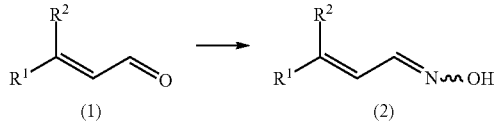

wherein $R^1$ and $R^2$ are as defined above.

[II-3] The process according to [II-2], wherein the oximating agent in the step (A) is hydroxylamine or a salt thereof.

[II-4] The process according to [II-2], wherein the oximating agent in the step (A) is hydroxylamine, hydroxylamine hydrochloride or hydroxylamine sulfate.

[II-5] The process according to any one of [II-2] to [II-4], wherein the reaction of the step (A) is performed in the presence of a base.

[II-6] The process according to [II-5], wherein the base in the step (A) is sodium hydroxide, potassium hydroxide, sodium carbonate, potassium carbonate, sodium hydrogen carbonate, potassium hydrogen carbonate or ammonia.

[II-7] The process according to any one of [II-2] to [II-6], wherein the reaction of the step (A) is performed in the presence of one or more (preferably one or two, more preferably two) solvents selected from water, acetonitrile, toluene, xylene, chlorobenzene, dichlorobenzene, and dichloromethane.

[II-8] The process according to any one of [II-2] to [II-6], wherein the reaction of the step (A) is performed in the presence of a solvent composed of a combination of water and dichlorobenzene (that is, a mixed solvent of water and dichlorobenzene).

[II-9] The process according to any one of [II-1] to [II-8], wherein the acid catalyst in the step (B) is one or more (preferably one to three, more preferably one or two, even more preferably one) acid catalyst(s) selected from the group consisting of mineral acids, carboxylic acids, sulfonic acids, phosphoric acids, and Lewis acids.

[II-10] The process according to any one of [II-1] to [II-8], wherein the acid catalyst in the step (B) is one or more (preferably one to three, more preferably one or two, even more preferably one) acid catalyst(s) selected from the group consisting of nitric acid, trifluoroacetic acid, trichloroacetic acid, maleic acid, maleic anhydride, benzenesulfonic acid, and p-toluenesulfonic acid.

[II-11] The process according to any one of [II-1] to [II-8], wherein the acid catalyst in the step (B) is trifluoroacetic acid or maleic acid.

[II-12] The process according to any one of [II-1] to [II-11], wherein the reaction of the step (B) is performed in the presence of 0.1 to 0.5 equivalents of a base catalyst based on 1 equivalent of the acid catalyst.

[II-13] The process according to [II-12], wherein the base catalyst in the step (B) is N-methylaniline, morpholine or pyrrolidine.

[II-14] The process according to any one of [II-1] to [II-13], wherein the reaction of the step (B) is performed in the presence of one or more (preferably one or two, more preferably one) solvent(s) selected from water, acetonitrile, toluene, xylene, chlorobenzene, dichlorobenzene, and dichloromethane.

[II-15] The process according to any one of [II-1] to [II-13], wherein the reaction of the step (B) is performed in the presence of a dichlorobenzene solvent.

[II-16] The process according to any one of [II-1] to [II-15], wherein the compound of the formula (2) is 3-methyl-2-butenal oxime and the compound of the formula (3) is 5,5-dimethyl-4,5-dihydroisoxazole.

Advantageous Effects of Invention

The present invention provides a novel process for producing the compound of the formula (3). According to the present invention, there is provided a process for producing the compound of the formula (3), which can overcome one or more of the disadvantages or problems of the prior art described above.

In the processes of JP 2013-512202 A (Patent Document 2), Synlett 2008, No. 6, 827-830 (Non-Patent Document 1) and Chem. Eur. J. 2010, Vol. 16, 11325-11339 (Non-Patent Document 2), a ketone oxime that forms a ketone such as acetone or diethyl ketone as a by-product was used as a raw material. However, according to the present invention, it has been found that ketone oximes are unnecessary. Thus, the process of the present invention does not produce ketones as by-products and/or wastes. In other words, it has been found that a raw material having a minimum structure necessary for introducing the oximino moiety (—O—N=) of the target compound is hydroxyamine (HO—NH$_2$). As a result, the present inventor has succeeded in producing the target compound without using any ketone oximes.

Therefore, according to the present invention, the production of by-products and/or wastes can be suppressed, and atom efficiency can be improved. Furthermore, according to the present invention, the target compound can be efficiently produced by a simple operation even if an inexpensive catalyst is used. As a result, according to the present invention, there has been provided a process that can easily and inexpensively produce, on an industrial scale, an intermediate for producing a herbicide such as pyroxasulfone. Therefore, the process of the present invention is industrially preferable, economical, and environmentally friendly, and has high industrial utility value.

DESCRIPTION OF EMBODIMENTS

The present invention will be described in detail below.
The terms and symbols used herein will be explained below.

Examples of the halogen atom include fluorine atom, chlorine atom, bromine atom and iodine.

(Ca-Cb) means that the number of carbon atoms is a to b. For example, "(C1-C4)" in "(C1-C4)alkyl" means that the number of the carbon atoms in the alkyl is 1 to 4.

Herein, it is to be understood that generic terms such as "alkyl" include both the straight chain and branched chain such as butyl and tert-butyl. However, when a specific term such as "butyl" is used, it is specific for "normal butyl", i.e., "n-butyl". In other words, the specific term "butyl" refers to "normal butyl", which is a straight chain. Branched chain isomers such as "tert-butyl" are referred to specifically when intended.

The prefixes "n-", "s-" and "sec-", "i-", "t-" and "tert-", "neo-", "c-" and "cyc-", "o-", "m-", and "p-" have their common meanings as follows: normal, secondary ("s-" and "sec-"), iso, tertiary ("t-" and "tert-"), neo, cyclo ("c-" and "cyc-"), ortho, meta, and para.

Herein, the following abbreviations may be used:
"Me" means methyl.
"Et" means ethyl. "Pr", "n-Pr" and "Pr-n" mean propyl (i.e., normal propyl).
"i-Pr" and "Pr-i" mean isopropyl.
"Bu", "n-Bu" and "Bu-n" mean butyl (i.e., normal butyl).
"s-Bu" and "Bu-s" mean sec-butyl.
"i-Bu" and "Bu-i" mean isobutyl.
"t-Bu" and "Bu-t" mean tert-butyl.
"Pen", "n-Pen" and "Pen-n" mean pentyl (i.e., normal pentyl).
"Hex", "n-Hex" and "Hex-n" mean hexyl (i.e., normal hexyl).
"Dec", "n-Dec" and "Dec-n" mean decyl (i.e., normal decyl).
"c-Pr" and "Pr-c" mean cyclopropyl.
"c-Bu" and "Bu-c" mean cyclobutyl.
"c-Pen" and "Pen-c" mean cyclopentyl.
"c-Hex" and "Hex-c" mean cyclohexyl.
"Ph" means phenyl.
"Bn" means benzyl.

"Ms" means methylsulfonyl (CH$_3$SO$_2$—).

"Ts" means tosyl (4-CH$_3$—C$_6$H$_4$SO$_2$—).

"Tf" means trifluoromethylsulfonyl (CF$_3$SO$_2$—).

"Ac" means acetyl (CH$_3$CO—).

The (C1-C6)alkyl means a straight or branched alkyl having 1 to 6 carbon atoms. Examples of the (C1-C6)alkyl include, but are not limited to, methyl, ethyl, propyl, isopropyl, butyl, sec-butyl, isobutyl, tert-butyl, pentyl, isopentyl, neopentyl, and hexyl.

The (C1-C4)alkyl means a straight or branched alkyl having 1 to 4 carbon atoms. Examples of the (C1-C4)alkyl include, but are not limited to, appropriate examples of the above-mentioned examples of the (C1-C6)alkyl.

The (C1-C6)haloalkyl means a straight or branched alkyl having 1 to 6 carbon atoms which is substituted with 1 to 13 same or different halogen atoms, wherein the halogen atoms have the same meaning as defined above. Examples of the (C1-C6)haloalkyl include, but are not limited to, fluoromethyl, difluoromethyl, trifluoromethyl, chlorodifluoromethyl, 2-fluoroethyl, 2-chloroethyl, 2,2,2-trifluoroethyl, pentafluoroethyl, 3-fluoropropyl, 3-chloropropyl, 2,2,3,3,3-pentafluoropropyl, 2,2,2-trifluoro-1-trifluoromethylethyl, heptafluoropropyl, 1,2,2,2-tetrafluoro-1-trifluoromethylethyl, 4-fluorobutyl, 4-chlorobutyl, 4-bromobutyl, 2,2,3,3,4,4,4-heptafluorobutyl, 5-fluoropenty, and 6-fluorohexyl.

The (C1-C4)haloalkyl means a straight or branched alkyl having 1 to 4 carbon atoms which is substituted with 1 to 9 same or different halogen atoms, wherein the halogen atoms have the same meaning as defined above. Examples of the (C1-C4)haloalkyl include, but are not limited to, appropriate examples of the above-mentioned examples of the (C1-C6) haloalkyl.

The (C3-C6)cycloalkyl means a cycloalkyl having 3 to 6 carbon atoms. Examples of the (C3-C6)cycloalkyl are cyclopropyl, cyclobutyl, cyclopentyl, and cyclohexyl.

The (C2-C6)alkenyl means a straight or branched alkenyl having 2 to 6 carbon atoms. Examples of the (C2-C6)alkenyl include, but are not limited to, vinyl, 1-propenyl, isopropenyl, 2-propenyl, 1-butenyl, 1-methyl-1-propenyl, 2-methyl-1-propenyl, 2-butenyl, 1,3-butadienyl, 1-pentenyl, and 1-hexenyl.

The (C2-C4)alkenyl means a straight or branched alkenyl having 2 to 4 carbon atoms. Examples of the (C2-C4)alkenyl include, but are not limited to, appropriate examples of the above-mentioned examples of the (C2-C6)alkenyl.

The (C2-C6)alkynyl means a straight or branched alkynyl having 2 to 6 carbon atoms. Examples of the (C2-C6)alkynyl include, but are not limited to, ethynyl, 1-propynyl, 2-propynyl, 1-butynyl, 1-methyl-2-propynyl, 2-butynyl, 1-pentynyl, and 1-hexynyl.

The (C2-C4)alkynyl means a straight or branched alkynyl having 2 to 4 carbon atoms. Examples of the (C2-C4)alkynyl include, but are not limited to, appropriate examples of the above-mentioned examples of the (C2-C6)alkynyl.

The (C1-C6)alkoxy means a (C1-C6)alkyl-O—, wherein the (C1-C6)alkyl moiety has the same meaning as defined above.

Examples of the (C1-C6)alkoxy include, but are not limited to, methoxy, ethoxy, propoxy, isopropoxy, butoxy, sec-butoxy, isobutoxy, tert-butoxy, pentyloxy, isopentyloxy, neopentyloxy, and hexyloxy.

The (C1-C4)alkoxy means (C1-C4)alkyl-O—, wherein the (C1-C4)alkyl moiety has the same meaning as defined above. Examples of the (C1-C4)alkoxy include, but are not limited to, appropriate examples of the above-mentioned examples of the (C1-C6)alkoxy.

The cyclic hydrocarbon group means a cyclic group which is aromatic or non-aromatic and is monocyclic or multicyclic, wherein all of the ring-constituting atoms are carbon atoms.

In one embodiment, examples of the cyclic hydrocarbon group include, but are not limited to, a 3- to 14-membered (preferably 5- to 14-membered, more preferably 5- to 10-membered) cyclic hydrocarbon group which is aromatic or non-aromatic and is monocyclic, bicyclic or tricyclic. In another embodiment, examples of the cyclic hydrocarbon group include, but are not limited to, a 4- to 8-membered (preferably 5- to 6-membered) cyclic hydrocarbon group which is aromatic or non-aromatic and is monocyclic or bicyclic (preferably monocyclic).

Examples of the cyclic hydrocarbon group include, but are not limited to, cycloalkyls and aryls.

The aryls are aromatic cyclic groups among the cyclic hydrocarbon groups as defined above.

The cyclic hydrocarbon group as defined or exemplified above may include a non-condensed cyclic group (e.g., a monocyclic group or a spirocyclic group) and a condensed cyclic group, when possible.

The cyclic hydrocarbon group as defined or exemplified above may be unsaturated, partially saturated or saturated, when possible.

The cyclic hydrocarbon group as defined or exemplified above is also referred to as a carbocyclic ring group.

The carbocyclic ring is a ring which corresponds to the cyclic hydrocarbon group as defined or exemplified above.

Herein, there are no particular limitations on the "substituent(s)" for the phrase "optionally substituted" as long as they are chemically acceptable and exhibit the effects of the present invention.

Herein, examples of the "substituent(s)" for the phrase "optionally substituted" include, but are not limited to, one or more substituents (preferably 1 to 4 substituents) selected independently from Substituent Group (a).

Substituent Group (a) is a group comprising a halogen atom; a nitro group; a cyano group; a hydroxy group; an amino group; (C1-C6)alkyl; (C1-C6)haloalkyl; (C3-C6)cycloalkyl; (C2-C6)alkenyl; (C2-C6)alkynyl; (C1-C6)alkoxy; phenyl; and phenoxy.

In addition, one or more substituents (preferably 1 to 4 substituents) selected independently from Substituent Group (a) may each independently have one or more substituents (preferably 1 to 4 substituents) selected independently from Substituent Group (b).

In this context, Substituent Group (b) is the same as Substituent Group (a).

Herein, a compound having isomers includes all of the isomers and any mixture thereof in any ratio.

For example, xylene includes o-xylene, m-xylene, p-xylene and any mixture thereof in any ratio.

For example, dichlorobenzene includes o-dichlorobenzene, m-dichlorobenzene, p-dichlorobenzene and any mixture thereof in any ratio.

For example, when a compound has geometric isomers (cis-trans isomers), the (E)-isomer (anti-isomer), the (Z)-isomer (syn-isomer) and a mixture thereof are included within the scope of the present invention. Specifically, for example, the compound of the formula (2):

[Chemical Formula 6]

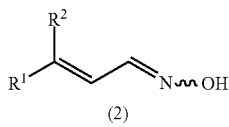

may be only a compound of the formula (2-E):

[Chemical Formula 7]

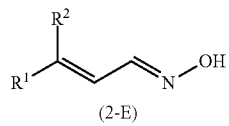

or may be only a compound of the formula (2-Z):

[Chemical Formula 8]

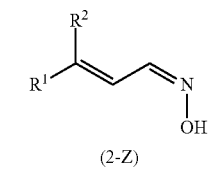

or may be any mixture of the compound of the above formula (2-E) and a compound of the above formula (2-Z) in any ratio.

The process of the present invention includes the following scheme, wherein $R^1$ and $R^2$ are as described in [1] above.

[Chemical Formula 9]

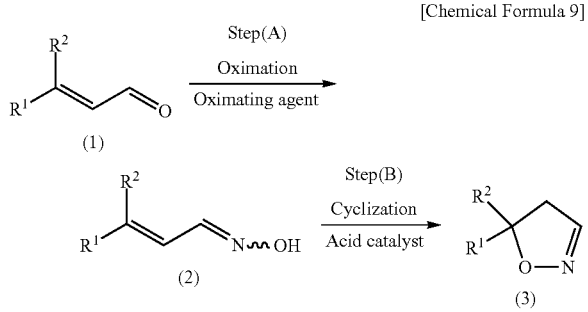

(Step (A))

The step (A) will be described.

The reaction of the step (A) is oximation.

The step (A) comprises reacting a compound of the formula (1) (β-disubstituted-α,β-unsaturated aldehyde) with an oximating agent to produce a compound of the formula (2) (β-disubstituted-α,β-unsaturated aldoxime),

[Chemical Formula 10]

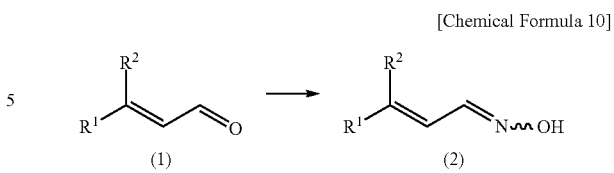

wherein $R^1$ and $R^2$ are as defined above.

(Raw Material in Step (A); Compound of Formula (1))

As a raw material in the step (A), a compound of the formula (1) is used. The compound of the formula (1) may be a known compound or can be produced from a known compound according to a known process.

Specific examples of the compound of the formula (1) include the following, but are not limited thereto; 3-methyl-2-buten-1-al (3-methyl-2-buten-1-al is also referred to as 3-methyl-2-butenal, 3-methylbut-2-enal or prenal), 3-methyl-2-penten-1-al, 3-ethyl-2-penten-1-al, 3,4-dimethyl-2-penten-1-al, 3,4,4-trimethyl-2-penten-1-al, 4-chloro-3-methyl-2-buten-1-al, 4,4,4-trifluoro-3-methyl-2-buten-1-al, 3-cyclopropyl-2-buten-1-al, 2-cyclobutylideneacetaldehyde, 2-cyclopentylideneacetaldehyde, 2-cyclohexylideneacetaldehyde, 3-methyl-2-hepten-1-al, 3,7-dimethyl-2,6-octadien-1-al, 3,7-dimethyl-2-octan-1-al, 2-(9H-fluoren-9-ylidene)acetaldehyde, 3,3-diphenyl-2-propen-1-al, 3,3-bis(4-phenyl)-2-propen-1-al, 3,3-bis(4-methoxyphenyl)-2-propen-1-al, 3,3-bis(4-methoxyphenyl)-2-propen-1-al, 3-phenyl-2-buten-1-al, 3-(4-methylphenyl)-2-buten-1-al, 3-(4-methoxyphenyl)-2-buten-1-al, and 3-(4-chlorophenyl)-2-buten-1-al. From the viewpoints of the usefulness of the product, etc., preferable specific examples of the compound of the formula (1) is 3-methyl-2-buten-1-al.

(Oximating Agent in Step (A))

The oximating agent to be used in the step (A) may be any oximating agent as long as the reaction proceeds. Examples of the oximating agent which can be used in the step (A) include, but are not limited to, hydroxylamine (free) and salts thereof. Examples of the hydroxylamine (free) include, but are not limited to, a 50% hydroxylamine aqueous solution, a 60% hydroxylamine aqueous solution, a 70% hydroxylamine aqueous solution, an 80% hydroxylamine aqueous solution, and a 90% hydroxylamine aqueous solution. Generally, the "50% hydroxylamine aqueous solution" is also referred to as "hydroxylamine (50% solution in water)". Examples of the hydroxylamine salt include, but are not limited to, hydroxylamine hydrochloride, hydroxylamine sulfate, hydroxylamine nitrate (e.g., 50% solution in water), hydroxylamine carbonate, hydroxylamine phosphate, hydroxylamine acetate, and hydroxylamine oxalate.

The oximating agent in the step (A) may be used alone or in combination of two or more kinds in any ratio. The form of the oximating agent in the step (A) may be any form as long as the reaction proceeds. Examples of the form include a solid of only an oximating agent or a liquid of only an oximating agent, and an aqueous solution with any concentration and a solution in a solvent other than water (e.g., an organic solvent) with any concentration. The form of the oximating agent in the step (A) can be selected appropriately by a person skilled in the art.

When hydroxylamine (free) is used as the oximating agent in the step (A), the form of the hydroxylamine may be any form as long as the reaction proceeds. In view of safety and economic efficiency, preferable examples of the form of the hydroxylamine (free) include an aqueous solution with a concentration of 10% or more and less than 70%, preferably an aqueous solution with a concentration of 45% or more and 55% or less.

From the viewpoints of safety, ease of handling, economic efficiency, etc., preferable examples of the oximating agent in the step (A) include hydroxylamine (free), hydroxylamine hydrochloride, and hydroxylamine sulfate, more preferably a 45% to 50% hydroxylamine aqueous solution, hydroxylamine hydrochloride, and hydroxylamine sulfate, even more preferably hydroxylamine hydrochloride and hydroxylamine sulfate, and further preferably hydroxylamine sulfate.

The amount of the oximating agent used in the step (A) may be any amount as long as the reaction proceeds. From the viewpoints of yield, suppression of by-products, economic efficiency, etc., in one embodiment, the amount may be, for example, in the range of 0.9 to 1.5 equivalents, preferably 0.9 to 1.2 equivalents based on 1 mol of the compound of the formula (1). In another embodiment, the amount may also be, for example, in the range of 1.0 to 1.5 equivalents, preferably 1.0 to 1.2 equivalents based on 1 mol of the compound of the formula (1). However, the amount can be adjusted appropriately by a person skilled in the art.

Accordingly, when hydroxylamine and/or a salt thereof is used as the oximating agent in the step (A), the amount of the hydroxylamine and/or the salt thereof may be any amount as long as the reaction proceeds. From the same viewpoints as described above, in one embodiment, the amount may be, for example, in the range of 0.9 to 1.5 mol, preferably 0.9 to 1.2 mol of hydroxylamine ($NH_2OH$) based on 1 mol of the compound of the formula (1). In another embodiment, the amount also may be, for example, in the range of 1.0 to 1.5 mol, preferably 1.0 to 1.2 mol, of hydroxylamine ($NH_2OH$) based on 1 mol of the compound of the formula (1). However, the amount can be adjusted appropriately by a person skilled in the art.

When hydroxylamine and/or a salt thereof is used as the oximating agent in the step (A), the reaction may be performed in the presence of an acid catalyst. Examples of the acid catalyst include, but are not limited to, hydrochloric acid, sulfuric acid, and acetic acid. The acid catalyst can be appropriately selected by a person skilled in the art. The amount of the acid catalyst used may be appropriately adjusted by a person skilled in the art. The acid catalyst may form a salt with hydroxylamine, and examples of the salt include, but are not limited to, hydroxylamine hydrochloride, hydroxylamine sulfate, and hydroxylamine acetate. The form of the acid catalyst can be appropriately selected by a person skilled in the art.

When a hydroxylamine salt (e.g., hydroxylamine hydrochloride, hydroxylamine sulfate, and hydroxylamine acetate) is used as the oximating agent in the step (A), the reaction may be performed in the presence of a base. Examples of the base include, but are not limited to, alkali metal hydroxides (e.g., lithium hydroxide, sodium hydroxide, and potassium hydroxide), alkaline earth metal hydroxides (e.g., magnesium hydroxide, calcium hydroxide, and barium hydroxide), alkali metal carbonates (e.g., lithium carbonate, sodium carbonate, and potassium carbonate), alkaline earth metal carbonates (e.g., magnesium carbonate, calcium carbonate, and barium carbonate), alkali metal hydrogen carbonates (e.g., lithium hydrogen carbonate, sodium hydrogen carbonate, and potassium hydrogen carbonate), alkali metal carboxylates (e.g., lithium acetate, sodium acetate, and potassium acetate), metal alkoxides (e.g., sodium methoxide, sodium ethoxide, and potassium tert-butoxide), amines (e.g., triethylamine, tributylamine, diisopropylethylamine, 1,8-diazabicyclo[5.4.0]-7-undec-7-ene (DBU), and pyridine), ammonia (e.g., 25 to 30% aqueous ammonia and ammonia gas, preferably 25 to 30% aqueous ammonia). Preferable examples of the base include sodium hydroxide, potassium hydroxide, sodium carbonate, potassium carbonate, sodium hydrogen carbonate, potassium hydrogen carbonate, and ammonia, more preferably include sodium hydroxide, sodium carbonate, sodium hydrogen carbonate, and ammonia, and even more preferably sodium hydroxide and ammonia. The bases may be used alone or in any combination of two or more kinds thereof in any ratio. The base may be in any form as long as the reaction proceeds. Examples of the form include a solid of only the base, a liquid of only the base, and a gas of only the base, an aqueous solution with any concentration, and a solution in a solvent other than water (e.g., an organic solvent) with any concentration. The form of the base can be appropriately selected by a person skilled in the art.

The amount of the base used in the step (A) may be any amount as long as the reaction proceeds. Examples of the amount of the base used include an amount in which the hydroxylamine salt can be neutralized to release free hydroxylamine. From the viewpoints of yield, suppression of by-products, economic efficiency, etc., 0.9 to 1.5 equivalents, preferably 0.9 to 1.1 equivalents, and more preferably 1.0 equivalent based on 1 equivalent of the hydroxylamine salt can be mentioned as examples. However, the amount can be adjusted appropriately by a person skilled in the art.

(Solvent in Step (A))

From the viewpoints of smooth progress of the reaction, etc., it is preferable to perform the reaction of the step (A) in the presence of a solvent. The solvent in the step (A) may be any solvent as long as the reaction of the step (A) proceeds. The solvent can be selected appropriately by a person skilled in the art. Examples of the solvent in the step (A) include, but are not limited to, water, alcohols (e.g., methanol, ethanol, 2-propanol, butanol, and tert-butanol (tert-butanol is also referred to as tert-butyl alcohol)), ethers (e.g., tetrahydrofuran (THF), 1,4-dioxane, diisopropyl ether, dibutyl ether, di-tert-butyl ether, cyclopentyl methyl ether (CPME), methyl tert-butyl ether, 1,2-dimethoxyethane (DME), diglyme, and triglyme), nitriles (e.g., acetonitrile), amides (e.g., N,N-dimethylformamide (DMF), N,N-dimethylacetamide (DMAC), and N-methylpyrrolidone (NMP)), alkyl ureas (e.g., N,N'-dimethylimidazolidinone (DMI)), sulfoxides (e.g., dimethyl sulfoxide (DMSO)), sulfones (e.g., sulfolane), carboxylic acid esters (e.g., ethyl acetate and butyl acetate), aromatic hydrocarbon derivatives (e.g., benzene, toluene, xylenes, chlorobenzene, dichlorobenzenes, and nitrobenzene), halogenated aliphatic hydrocarbons (e.g., dichloromethane, chloroform, and 1,2-dichloroethane (EDC)), aliphatic hydrocarbons (e.g., hexane, heptane, octane, cyclohexane, and ethylcyclohexane), and any combination thereof in any ratio.

From the viewpoints of reactivity, yield, economic efficiency, etc., in one embodiment, preferable examples of the solvent in the step (A) include water, alcohols, nitriles, ethers, aromatic hydrocarbon derivatives, halogenated aliphatic hydrocarbons, and any combination thereof in any ratio, more preferably water, nitriles, aromatic hydrocarbon derivatives, halogenated aliphatic hydrocarbons, and any combination thereof in any ratio, even more preferably water, aromatic hydrocarbon derivatives, halogenated aliphatic hydrocarbons, and any combination thereof in any ratio, still even more preferably water, halogenated aliphatic hydrocarbons, and any combination thereof in any ratio, and particularly preferably any combination of water and a halogenated aliphatic hydrocarbon in any ratio. Preferable specific examples of the solvent in the step (A) include water, methanol, ethanol, 2-propanol, tert-butanol, acetonitrile, tetrahydrofuran (THF), toluene, xylene, chlorobenzene, dichlorobenzene, dichloromethane, and any combination thereof in any ratio, more preferably water, acetonitrile, toluene, xylene, chlorobenzene, dichlorobenzene, dichloromethane, and any combination thereof in any ratio, even more preferably water, toluene, xylene, chlorobenzene, dichlorobenzene, dichloromethane, and any combination thereof in any ratio, still even more preferably water, dichloromethane, and any combination thereof in any ratio, and particularly preferably any combination of water and dichloromethane in any ratio. In any case, the presence of water is preferred. In another embodiment, preferable examples of the solvent in the step (A) include water, alcohols, nitriles, ethers, aromatic hydrocarbon derivatives, halogenated aliphatic hydrocarbons, and any combination thereof in any ratio, more preferably water, alcohols, nitriles, halogenated aliphatic hydrocarbons, and any combination thereof in any ratio, even more preferably water, nitriles, halogenated aliphatic hydrocarbons, and any combination thereof in any ratio, still even more preferably water, halogenated aliphatic hydrocarbons, and any combination thereof in any ratio, and particularly preferably any combination of water and a halogenated aliphatic hydrocarbon in any ratio. Preferable specific examples of the solvent in the step (A) include water, methanol, ethanol, 2-propanol, tert-butanol, acetonitrile, tetrahydrofuran (THF), toluene, xylene, chlorobenzene, dichlorobenzene, dichloromethane, and any combination thereof in any ratio, more preferably water, methanol, ethanol, 2-propanol, tert-butanol, acetonitrile, dichloromethane, and any combination thereof in any ratio, even more preferably water, acetonitrile, dichloromethane, and any combination thereof in any ratio, still even more preferably water, dichloromethane, and any combination thereof in any ratio, and particularly preferably any combination of water and dichloromethane in any ratio. In any case, the presence of water is preferred.

The amount of the solvent used in the step (A) may be any amount as long as the reaction system can be sufficiently stirred. From the viewpoints of yield, suppression of by-products, economic efficiency, etc., the amount may be, for example, in the range of 0 (zero) to 10 L (liters), preferably 0.02 to 5 L, more preferably 0.02 to 1 L, and even more preferably 0.1 to 1 L based on 1 mol of the compound of the formula (1). However, the amount can be adjusted appropriately by a person skilled in the art. When a combination of two or more solvents is used, the ratio of the two or more solvents may be any ratio as long as the reaction proceeds. The ratio can be adjusted appropriately by a person skilled in the art. The solvent may be in a single layer or may be separated into two layers as long as the reaction proceeds.

(Reaction Temperature in Step (A))

The reaction temperature in the step (A) is not particularly limited. From the viewpoints of yield, suppression of by-products, economic efficiency, etc., the reaction temperature may be, for example, in the range of −30° C. (minus 30° C.) to 160° C., preferably −10° C. to 80° C., more preferably 0° C. to 80° C., even more preferably 10° C. to 50° C., and still even more preferably room temperature (10° C. to 35° C.). However, the reaction temperature can be adjusted appropriately by a person skilled in the art.

(Reaction Time in Step (A))

The reaction time in the step (A) is not particularly limited. From the viewpoints of yield, suppression of by-products, economic efficiency, etc., the reaction time may be, for example, in the range of 0.5 hours to 48 hours, preferably 0.5 hours to 24 hours, and more preferably 1 hour to 12 hours. However, the reaction time can be adjusted appropriately by a person skilled in the art.

(Product in Step (A): Compound of Formula (2))

The product in the step (A) is an oxime corresponding to the compound of the formula (1) used as a raw material.

Specific examples of the compound of the formula (2) include the following, but are not limited thereto; 3-methyl-2-buten-1-al oxime (3-methyl-2-buten-1-al oxime is also referred to as 3-methyl-2-butenal oxime, 3-methylbut-2-enal oxime or prenal oxime), 3-methyl-2-penten-1-al oxime, 3-ethyl-2-penten-1-al oxime, 3,4-dimethyl-2-penten-1-al oxime, 3,4,4-trimethyl-2-penten-1-al oxime, 4-chloro-3-methyl-2-buten-1-al oxime, 4,4,4-trifluoro-3-methyl-2-buten-1-al oxime, 3-cyclopropyl-2-buten-1-al oxime, 2-cyclobutylideneacetaldoxime, 2-cyclopentylideneacetaldoxime, 2-cyclohexylideneacetaldoxime, 3-methyl-2-hepten-1-al oxime, 3,7-dimethyl-2,6-octadien-1-al oxime, 3,7-dimethyl-2-octan-1-al oxime, 2-(9H-fluoren-9-ylidene)acetaldoxime, 3,3-diphenyl-2-propen-1-al oxime, 3,3-bis(4-phenyl)-2-propen-1-al oxime, 3,3-bis(4-methoxyphenyl)-2-propen-1-al oxime, 3,3-bis(4-methoxyphenyl)-2-propen-1-al oxime, 3-phenyl-2-buten-1-al oxime, 3-(4-methylphenyl)-2-buten-1-al oxime, 3-(4-methoxyphenyl)-2-buten-1-al oxime, and 3-(4-chlorophenyl)-2-buten-1-al oxime. From the viewpoints of the usefulness of the product, etc., preferable specific examples of the compound of the formula (2) is 3-methyl-2-buten-1-al oxime (3-methyl-2-butenal oxime).

The compound of the formula (2), which is the product in the step (A), can be used as a raw material in the step (B). The compound of the formula (2) to be obtained in the step (A) may be used for the next step after isolation, or may be used for the next step after further purification, or may be used for the next step without isolation.

(Step (B))

The step (B) will be described.

The reaction of the step (B) is a cyclization reaction. The step (B) is the step of reacting a compound of the formula (2) (β-disubstituted-α,β-unsaturated aldoxime) in the presence of an acid catalyst to produce a compound of the formula (3). The reaction may be performed in the presence of a base catalyst in addition to the acid catalyst,

[Chemical Formula 11]

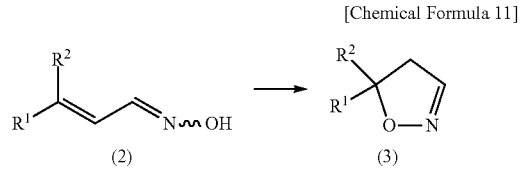

wherein $R^1$ and $R^2$ are as defined above.

(Raw Material of Step (B); Compound of Formula (2))

A compound of the formula (2) is used as a raw material in the step (B). The compound of the formula (2) may be a known compound or may be produced from a known compound according to a known process. In addition, the compound of the formula (2) can be produced by the process of the above step (A). Specific examples and preferable specific examples of the compound of the formula (2) are as described above.

(Acid Catalyst in Step (B))

An acid catalyst is essential in the reaction of the step (B). The acid catalyst in the step (B) may be any acid catalyst as long as the reaction proceeds. In addition, as long as the reaction proceeds, any of the following forms may be used and are included within the scope of the present invention. A free acid can be used as the acid catalyst. The acid catalyst may be used in the form of a salt. When the acid catalyst is a salt, the acid catalyst may be a simple salt or a double salt. The acid catalyst may be used in the form of an anhydride. The acid catalyst may be used in the form of a hydrate. The acid catalyst may be used in the form of a dimer or the like.

Examples of the acid catalyst in the step (B) include the following, but are not limited thereto.

a) Mineral Acids

As the acid catalyst in the step (B), a mineral acid can be used. Examples of the mineral acid include hydrochloric acid, sulfuric acid, and nitric acid.

b) Carboxylic Acids

As the acid catalyst in the step (B), a carboxylic acid, a salt thereof, and an anhydride thereof can be used.

Therefore, the carboxylic acid may be used in the form of a free acid or in the form of a salt thereof. In addition, the carboxylic acid may be used in the form of an anhydride thereof.

In one embodiment, examples of the carboxylic acid include saturated or unsaturated aliphatic(C1-C8) monocarboxylic, dicarboxylic, and tricarboxylic acids optionally substituted by one or more halogen atoms, and aromatic(C7-C11) monocarboxylic, dicarboxylic, and tricarboxylic acids optionally substituted by one or more substituents independently selected from halogen atoms, (C1-C4)alkyl, and (C1-C4)haloalkyl. Examples of preferable carboxylic acids include saturated or unsaturated aliphatic(C1-C8) carboxylic acids optionally substituted by one or more halogen atoms. Examples of the carboxylic acid salt and carboxylic anhydride are their salts and anhydrides. In another embodiment, examples of the carboxylic acid include saturated or unsaturated aliphatic(C1-C8) carboxylic acids optionally substituted by one or more halogen atoms, and benzoic acid optionally substituted by one or more substituents independently selected from halogen atoms, (C1-C4)alkyl, and (C1-C4)haloalkyl. Examples of preferable carboxylic acids include saturated or unsaturated aliphatic(C1-C8) carboxylic acids optionally substituted by one or more halogen atoms. Examples of the carboxylic acid salt and carboxylic anhydride are their salts and anhydrides.

Specific examples of the carboxylic acid include acetic acid, trifluoroacetic acid, trichloroacetic acid, dichloroacetic acid, maleic acid, citric acid, benzoic acid, and phthalic acid. Specific examples of preferable carboxylic acids include trifluoroacetic acid, trichloroacetic acid, dichloroacetic acid, and maleic acid. Specific examples of the carboxylic acid salt include ammonium trifluoroacetate ($CF_3COO^-NH_4^+$)) and N-methylanilium trifluoroacetate ($CF_3COO^-C_6H_5N^+$ $(CH_3)H_2$). Specific examples of the carboxylic anhydride include trifluoroacetic anhydride, maleic anhydride, and phthalic anhydride. Specific examples of preferable carboxylic anhydrides include maleic anhydride.

c) Sulfonic Acids

As the acid catalyst in the step (B), a sulfonic acid, a salt thereof and an anhydride thereof can be used.

Therefore, the sulfonic acid may be used in the form of a free acid or in the form of a salt thereof. In addition, the sulfonic acid may be used in the form of the anhydride thereof. Examples of the sulfonic acid include methanesulfonic acid, trifluoromethanesulfonic acid (TfOH), benzenesulfonic acid, p-toluenesulfonic acid (including p-toluenesulfonic acid monohydrate ($TsOH\cdot H_2O$)), and 10-camphorsulfonic acid. Examples of the sulfonic acid salt include pyridinium p-toluenesulfonate (PPTS). Examples of the sulfonic anhydride include methanesulfonic anhydride and trifluoromethanesulfonic anhydride.

d) Phosphoric Acids

As the acid catalyst in the step (B), phosphoric acids can be used. The phosphoric acids are phosphoric acid and derivatives thereof. The phosphoric acids are not particularly limited as long as they are chemically acceptable and exhibit the effects of the present invention. Examples of the phosphoric acid include the following, but are not limited thereto.

d-1) Phosphoric Acid, and Salts and Anhydride Thereof

Phosphoric acid may be used in the form of a free acid or in the form of a salt thereof. In addition, phosphoric acid may be used in the form of the anhydride thereof. Examples of the phosphoric acid and salts and anhydride thereof include phosphoric acid (orthophosphoric acid; $B_3PO_4$), ammonium dihydrogen phosphate, polyphosphoric acid, pyrophosphoric acid (diphosphoric acid), and diphosphorus pentoxide.

d-2) Phosphoric Acid Monoester, and Salts and Anhydride Thereof

The phosphoric acid monoester may be used in the form of a free acid or in the form of a salt thereof. The phosphoric acid monoester may be used in the form of its anhydride as long as it is chemically acceptable. Examples of the phosphoric acid monoester include ethyl phosphate (i.e., ethyl dihydrogen phosphate; $(C_2H_5O)P(=O)(OH)_2$) and phenyl phosphate (i.e., phenyl dihydrogen phosphate; $(C_5H_5O)P(=O)(OH)_2$).

d-3) Phosphoric Diester, and Salts and Anhydrides Thereof

The phosphoric diester may be used in the form of a free acid or in the form of a salt thereof. The phosphoric diester may be used in the form of its anhydride as long as it is chemically acceptable. Examples of the phosphoric diesters include diethyl phosphate (i.e., diethyl hydrogen phosphate; $(C_2H_5O)_2P(=O)OH$) and diphenyl phosphate (i.e., diphenyl hydrogen phosphate; $(C_5H_5O)_2P(=O)OH$). Examples of the phosphoric diester salt include diphenyl N-methylanilinium phosphate $((C_5H_5O)_2P(=O)O^{-C}{}_6H_5N^+(CH_3)H_2)$.

e) Lewis Acids

As the acid catalyst in the step (B), a Lewis acid can be used. Examples of the Lewis acid include the following, but are not limited thereto.

e-1) In one embodiment, examples of the Lewis acid include, but are not limited to, compounds formed from cations and anions. The cation forming the Lewis acid may be either a single species or in combination of two or more species. The anion forming the Lewis acid may be either a single species or in combination of two or more species.

The Lewis acid formed from a cation and an anion may include components other than the cation and the anion.

Examples of the cation that form the Lewis acid include cations of the elements of Groups 1, 2, 3 (including lanthanoids), 4, 5, 6, 7, 8, 9, 10, 11, 12, 13, 14, and 15 on the long-form periodic table.

Herein, as to the long-form periodic table, reference may be made to the following, for example.

IUPAC Periodic Table of the Elements, dated 28 Nov. 2016. https://www.iupac.org/cms/wp-content/uploads/2015/07/IUPAC_Periodic_Table-28Nov16.pdf Examples of the cation of the element of Groups 1 to 15 on the long-form periodic table include the following, but are not limited thereto.

Examples of the cation of Group 1 elements include the following: ions of lithium (Li), sodium (Na), potassium (K) or cesium (Cs).

Examples of the cation of Group 2 elements include the following: ions of magnesium (Mg), calcium (Ca) or barium (Ba).

Examples of the cation of Group 3 elements include the following: ions of scandium (Sc), yttrium (Y), lanthanum (La), cerium (Ce), samarium (Sm) or ytterbium (Yb).

Examples of the cation of Group 4 elements include the following: ions of titanium (Ti), zirconium (Zr) or hafnium (Hf).

Examples of the cation of Group 5 elements include the following: ions of vanadium (V).

Examples of the cation of Group 6 elements include the following: molybdenum ion (Mo) or ions of tungsten (W).

Examples of the cation of Group 7 elements include the following: ions of manganese (Mn).

Examples of the cation of Group 8 elements include the following: ions of iron (Fe) or ruthenium (Ru).

Examples of the cation of Group 9 elements include the following: ions of cobalt (Co), rhodium (Rh) or iridium (Ir).

Examples of the cation of Group 10 elements include the following: ions of nickel (Ni), palladium (Pd) or platinum (Pt).

Examples of the cation of Group 11 elements include the following: ions of copper (Cu), silver (Ag) or gold (Au).

Examples of the cation of Group 12 elements (i.e., zinc group metals) include the following: ions of zinc.

Examples of the cation of Group 13 (i.e., earth metal) elements include the following: ions of boron (B), aluminum (Al), gallium (Ga), or indium (In).

Examples of the cation of Group 14 elements include the following: ions of germanium (Ge) or tin (Sn).

Examples of the cation of Group 15 elements include the following: ions of bismuth.

Preferable examples of the cation include the following, but are not limited thereto;
ions of magnesium (Mg), calcium (Ca), scandium (Sc), ytterbium (Yb), iron (Fe), cobalt (Co), nickel (Ni), palladium (Pd), platinum (Pt), copper (Cu), silver (Ag), gold (Au), zinc, boron (B), aluminum (Al), and tin (Sn).

Specific examples of the cation of the element of Groups 1 to 15 on the long-form periodic table include the following, but are not limited thereto.

Specific examples of the cation of Group 1 elements (i.e., alkali metals) include the following: lithium ion ($Li^+$), sodium ion ($Na^+$), potassium ion ($K^+$), and cesium ion ($Cs^+$).

Specific examples of the cation of Group 2 elements (i.e., alkaline earth metals) include the following: magnesium ion ($Mg^{2+}$), calcium ion ($Ca^{2+}$), and barium ion ($Ba^{2+}$).

Specific examples of the cation of Group 3 (including lanthanoids) elements include the following: scandium ion ($Sc^{3+}$), yttrium ion ($Y^{3+}$), lanthanum ion ($La^{3+}$), cerium(III) ion ($Ce^{3+}$), cerium(IV) ion ($Ce^{4+}$), samarium(II) ion ($Sm^{2+}$), samarium(III) ion ($Sm^{3+}$), and ytterbium(III) ion ($Yb^{3+}$).

Specific examples of the cation of Group 4 elements include the following: titanium(III) ion ($Ti^{3+}$), titanium(IV) ion ($Ti^{4+}$), zirconium(IV) ion ($Zr^{4+}$), and hafnium(IV) ion ($Hf^{4+}$).

Specific examples of the cation of Group 5 elements include the following: vanadium(II) ion ($V^{2+}$), vanadium(III) ion ($V^{3+}$), vanadium(IV) ion ($V^{4+}$), and vanadium(V) ion ($V^{5+}$), and specific examples of the cation of Group 6 elements include the following: molybdenum(IV) ion ($Mo^{4+}$), molybdenum(VI) ion ($Mo^{6+}$), and tungsten(VI) ion ($W^{6+}$).

Specific examples of the cation of Group 7 elements include the following: manganese(II) ion ($Mn^{2+}$), manganese(IV) ion ($Mn^{4+}$), and manganese(VII) ion ($Mn^{7+}$).

Specific examples of the cation of Group 8 elements include the following:
iron(II) ion ($Fe^{2+}$), iron(III) ion ($Fe^{3+}$), and ruthenium(III) ion ($Ru^{3+}$).

Specific examples of the cation of Group 9 elements include the following: cobalt(II) ion ($Co^{2+}$), cobalt(III) ion ($Co^{3+}$), rhodium(II) ion ($Rh^{2+}$), rhodium(III) ion ($Rh^{3+}$), and iridium(III) ions ($Ir^{3+}$).

Specific examples of the cation of Group 10 elements include the following: nickel(II) ion ($Ni^{2+}$), palladium(II) ion ($Pd^{2+}$), and platinum(II) ion ($Pt^{2+}$).

Specific examples of the cation of Group 11 elements include the following: copper(I) ion ($Cu^+$), copper(II) ion ($Cu^{2+}$), silver(I) ion ($Ag^+$), gold(I) ion ($Au^+$), and gold(III) ion ($Au^{3+}$).

Specific examples of the cation of Group 12 elements (i.e., zinc group metals) include the following: zinc ion ($Zn^{2+}$).

Specific examples of the cation of Group 13 elements (i.e., earth metals) include the following: boron ion ($B^{3+}$), aluminum ion ($Al^{3+}$), gallium(III) ion ($Ga^{3+}$), and indium (III) ion ($In^{3+}$).

Specific examples of the cation of Group 14 elements include the following: germanium(II) ion ($Ge^{2+}$), germanium(IV) ion ($Ge^{4+}$), tin(II) ion ($Sn^{2+}$), and tin(IV) ion ($Sn^{4+}$).

Specific examples of the cation of Group 15 elements include the following: bismuth(III) ion ($Bi^{3+}$).

Preferable specific examples of the cation include the following: magnesium ion ($Mg^{2+}$), calcium ion ($Ca^{2+}$), scandium ion ($Sc^{3+}$), ytterbium(III) ion ($Yb^{3+}$), iron(II) ion ($Fe^{2+}$), iron (III) ion ($Fe^{3+}$), cobalt (II) ion ($Co^{2+}$), cobalt(III) ion ($Co^{3+}$), nickel(II) ion ($Ni^{2+}$), palladium(II) ion ($Pd^{2+}$), platinum(II) ion ($Pt^{2+}$), copper(I) ion ($Cu^+$), copper(II) ion ($Cu^{2+}$), silver(I) ion ($Ag^+$), gold(I) ion ($Au^+$), zinc ion ($Zn^{2+}$), boron ion ($B^{3+}$), aluminum Ion ($Al^{3+}$), tin(II) ion ($Sn^{2+}$), and tin(IV) ion ($Sn^{4+}$).

More preferable specific examples of the cation include the following: calcium ion ($Ca^{2+}$),
copper(II) ion ($Cu^{2+}$), and silver(I) ion ($Ag^+$).

Other preferable examples of the cation include transition metal ions. Herein, the transition metal ions are the cations of the elements of Group 3 (including lanthanoids) to Group 11 on the long-form periodic table. Accordingly, examples of the transition metal ions include the cations of the elements belonging to Group 3 (including lanthanoids) to Group 11.

Preferable examples of the transition metal ion include the following, but are not limited thereto;
ions of scandium (Sc), ytterbium (Yb),
iron (Fe),
cobalt (Co),
nickel (Ni), palladium (Pd), platinum (Pt),
copper (Cu), silver (Ag), and gold (Au).

Specific examples of the transition metal ion include the specific examples of the cation of the element belonging to Group 3 (including lanthanoids) to Group 11.

Preferred specific examples of the transition metal ion include
scandium ion ($Sc^{3+}$), ytterbium(III) ion ($Yb^{3+}$),
iron(II) ion ($Fe^{2+}$), iron(III) ion ($Fe^{3+}$),
cobalt(II) ion ($Co^{2+}$), cobalt(III) ion ($Co3+$),
nickel(II) ion ($Ni^{2+}$), palladium(II) ion ($Pd^{2+}$),
platinum(II) ion ($Pt^{2+}$), copper(I) ion (Cu$^+$), copper(II) ion (Cu$^{2+}$), silver(I) ion (Ag$^+$), and gold(I) ion (Au$^+$).

More preferable specific examples of the transition metal ion include
copper(II) ion (Cu$^{2+}$) and silver(I) ion (Ag$^+$).
Further preferable specific examples of the transition metal ion include copper(II) ion (Cu$^{2+}$).

Examples of the anion to form the Lewis acid include the following, but are not limited thereto;
halide ions (e.g., fluoride ion (F$^-$), chloride ion (Cl$^-$), bromide ion (Br$^-$), and iodide ion (I$^-$)),
sulfate ion (SO$_4^{2-}$), nitrate ion (NO$_3^-$), oxide ion (O$^{2-}$), perchlorate ion (ClO$_4^-$), tetrafluoroborate ion (BF$_4^-$), hexafluorophosphate ion (PF$_6^-$), and hexafluoroantimonate ion (SbF$_6^-$),
carboxylic acid ions (e.g., acetate ion (CH$_3$CO$_2^-$; AcO$^-$) and trifluoroacetate ion (CF$_3$CO$_2^-$)),
sulfonate ions (e.g., methanesulfonate ion (CH$_3$SO$_3^-$; MsO$^-$; also referred to as mesylate ion),
trifluoromethanesulfonate ion (CF$_3$SO$_3^-$; TfO$^-$; also referred to as triflate ion), heptadecafluorooctanesulfonate ion (C$_8$F$_{17}$SO$_3^-$; also referred to as perfluorooctanesulfonate ion), benzenesulfonate ion (C$_6$H$_5$SO$_3^-$; also referred to as besylate ion), p-toluenesulfonic acid ion (4-CH$_3$—C$_6$H$_4$SO$_3^-$; TsOH$^-$; also referred to as tosylate ion)), bis(trifluoromethylsulfonyl)imide ion ((CF$_3$SO$_2$)$_2$N$^-$; Tf$_2$N$^-$; also referred to as bis(trifluoromethylsulfonyl)amide ion), and
alkoxide ions (e.g., methoxide ion (CH$_3$O$^-$; MeO$^-$), ethoxide ion (C$_2$H$_5$O$^-$; EtO$^-$), and isopropoxide ion ((CH$_3$)$_2$CHO$^-$; i-PrO$^-$).

Preferred examples of the anion to form the Lewis acid include:
fluoride ion (F$^-$), chloride ion (Cl$^-$), bromide ion (Br$^-$), iodide ion (I$^-$)),
trifluoromethanesulfonic acid ion (CF$_3$SO$_3^-$; TfO$^-$; also called triflate ion), and bis(trifluoromethylsulfonyl)amide ion ((CF$_3$SO$_2$)$_2$N$^-$; Tf$_2$N$^-$).

e-2) In another embodiment, examples of the Lewis acid include, but are not limited to, compounds of the following formula:

$$MZn$$

wherein M is a cation of the element of Group 1, 2, 3, (including lanthanoids), 4, 5, 6, 7, 8, 9, 10, 11, 12, 13, 14, or 15 on the long-form periodic table),
Z is the same or different and is a counter anion of M, and n is an integer of 1 to 4.

The Lewis acid of the above formula may include components other than Z and M.

Examples of the cation of the element of Groups 1 to 15 on the long-form periodic table in e-2 are the same as those in the above e-1. Preferable examples of the cation in the e-2 are the same as those in the above e-1. Specific examples of the cation of the element of Groups 1 to 15 on the long-form periodic table in e-2 are the same as those in the above e-1. Preferable specific examples of the cation of the element of Groups 1 to 15 on the long-form periodic table in e-2 are the same as those in the above e-1. More preferable specific examples of the cation of the element of Groups 1 to 15 on the long form periodic table in e-2 are the same as those in the above e-1.

Other preferable examples of the cation in e-2 are the same as those in the above e-1 and include transition metal ions. Examples of the transition metal ion in e-2 are the same as those in the above e-1. Preferable examples of the transition metal ion in e-2 are the same as those in the above e-1. Specific examples, preferable specific examples, and more preferable specific examples of the transition metal ion in e-2 are the same as those in the above e-1.

Examples of Z are the same as the examples of the anion forming the Lewis acid in the above e-1. Examples of preferred anion in e-2 are the same as those in the above e-1. Examples of more preferred anion in e-2 are the same as those in the above e-1.

For the above e-1 and e-2, specific examples of Lewis acid include the following, but are not limited thereto;
lithium bromide (LiBr), lithium perchlorate (LiClO$_4$), sodium bromide (NaBr), potassium bromide (KBr), cesium bromide (CsBr), magnesium chloride (MgCl$_2$), magnesium bromide (MgBr$_2$), magnesium triflate (Mg(OTf)$_2$), magnesium bis(trifluoromethanesulfonyl)imide (Mg(NTf$_2$)$_2$), calcium chloride (CaCl$_2$), calcium bromide (CaBr$_2$) (including hydrate), calcium triflate (Ca(OTf)$_2$), calcium bis(trifluoromethanesulfonyl)imide (Ca(NTf$_2$)$_2$), scandium(III) chloride (ScCl$_3$), scandium(III) triflate (Sc(OTf)$_3$) (scandium(III) triflate is also called scandium(III) trifluoromethanesulfonate (Sc(OSO$_2$CF$_3$)$_3$)), scandium(III) heptadecafluorooctanesulfonate (Sc(OSO$_2$C$_8$F$_{17}$)$_3$) (scandium(III) heptadecafluorooctanesulfonate is also called scandium(III) perfluorooctanesulfonate), scandium(III) bis(trifluoromethanesulfonyl)imide (Sc(III) (NTf$_2$)$_3$), yttrium(III) chloride (YCl$_3$), yttrium(III) triflate (Y(OTf)$_3$), lanthanum(III) chloride (LaCl$_3$), lanthanum(III) triflate (La(OTf)$_3$), cerium(III) chloride (CeCl$_3$), cerium(III) triflate (Ce(OTf)$_3$), samarium(III) chloride (SmCl$_3$), samarium(III) triflate (Sm(OTf)$_3$), ytterbium(III) chloride (YbCl$_3$), ytterbium(III) triflate (Yb(OTf)$_3$), titanium(IV) chloride (TiCl$_4$), tetramethoxytitanium(IV) (Ti(OMe)$_4$) (tetramethoxytitanium(IV) is also called titanium(IV) tetramethoxide), tetraisopropoxytitanium(IV) (Ti(OPr-i)$_4$) (tetraisopropoxytitanium (IV) is also called titanium(IV) tetraisopropoxide), zirconium(IV) chloride (ZrCl$_4$), hafnium(IV) tetraflate (Hf(OTf)$_4$), hafnium(IV) heptadecafluorooctanesulfonate (Hf(OSO$_2$C$_8$F$_{17}$)$_4$), vanadium(III) chloride (VCl$_3$), vanadium(V) oxide (V$_2$O$_5$), manganese(II) chloride (MnCl$_2$) (including tetrahydrate), manganese(II) sulfate (MnSO$_4$) (including pentahydrate), iron(II) chloride (FeCl$_2$) (including tetrahydrate), iron(II) acetate (Fe(OAc)$_2$), iron(II) triflate (Fe(OTf)$_2$), iron(III) chloride (FeCl$_3$), iron(III) bromide (FeBr$_3$), iron(III) triflate (Fe(OTf)$_3$), ruthenium(III) chloride (RuCl$_3$), cobalt(II) chloride (CoCl$_2$) (including hexahydrate), cobalt(II) sulfate (CoSO$_4$) (including heptahydrate), cobalt(II) acetate, (Co (OAc)$_2$) (including tetrahydrate), rhodium(II) acetate (Rh(OAc)$_2$) (including hydrate and dimer), rhodium(III) chloride (RhCl$_3$) (including trihydrate), iridium(III) chloride (IrCl$_3$), nickel(II) chloride (NiCl$_2$) (including hexahydrate), nickel(II) acetate, (Ni(OAc)$_2$) (Including tetrahydrate), nickel(II) triflate (Ni(OTf)$_2$), palladium(II) chloride (PdCl$_2$), palladium(II) acetate, (Pd(OAc)$_2$), platinum(II) chloride (PtCl$_2$), copper(I) chloride (CuCl), copper(I) bromide (CuBr), copper(I) iodide (CuI), copper(I) triflate benzene complex (CuOTf.C$_6$H$_6$), copper(I) triflate toluene complex (CuOTf.C$_6$H$_5$CH$_3$), copper(II) chloride (CuCl$_2$) (including dihydrate), copper(II) bromide (CuBr$_2$), copper(II) acetate (Cu(OAc)$_2$), copper(II) triflate (Cu(OTf)$_2$) (copper(II) triflate is also called copper(II) trifluoromethanesulfonate (Cu(OSO$_2$CF$_3$)$_2$)), copper(II) bis(trifluoromethanesulfonyl)imide (Cu(NTf$_2$)$_2$), silver chloride (AgCl), silver(I) triflate (AgOTf), zinc chloride (ZnCl$_2$), zinc bromide (ZnBr$_2$), zinc iodide (ZnI$_2$), zinc(II) triflate (Zn(OTf)$_2$), boron trifluoride ethyl ether complex (BF$_3$.OEt$_2$), boron trifluoride butyl ether complex (BF$_3$.n-Bu$_2$O), boron trifluoride tetrahydrofuran ether complex (BF₃.THF), boron trifluoride methanol complex (BF₃.MeOH), boron trifluoride acetonitrile complex (BF₃.MeCN), trimethoxyborane (B(OMe)₃), aluminum chloride (AlCl₃), aluminum bromide (AlBr₃), trimethoxyaluminum (Al(OMe)₃), gallium(III) chloride (GaCl₃), indium(III) chloride (InCl₃), germanium(II) chloride (GeCl₂), germanium(IV) chloride (GeCl₄), bismuth(III) chloride (BiCl₃), bismuth(III) triflate (Bi(OTf)₃), tin(II) chloride (SnCl₂), tin(II) triflate (Sn(OTf)₂), and tin(IV) chloride (SnCl₄).

For e-1 and e-2 above, preferred specific examples of Lewis acid include the following:
magnesium triflate (Mg(OTf)₂), magnesium bis(trifluoromethanesulfonyl)imide (Mg(NTf₂)₂), calcium triflate (Ca(OTf)₂), calcium bis (trifluoromethanesulfonyl) imide (Ca(NTf₂)₂), scandium(III) triflate (Sc(OTf)₃), titanium(IV) chloride (TiCl₄), tetramethoxytitanium(IV) (Ti(OMe)₄), tetraisopropoxytitanium(IV) (Ti(OPr-i)₄), iron(III) chloride (FeCl₃), iron(III) bromide (FeBr₃), iron(III) triflate (Fe(OTf)₃), nickel(II) chloride (NiCl₂) (including hexahydrate), nickel(II) acetate, (Ni(OAc)₂) (including tetrahydrate), nickel(II) triflate (Ni(OTf)₂), copper(I) chloride (CuCl), copper(I) bromide (CuBr), copper(I) iodide (CuI), copper(I) triflate benzene complex (CuOTf.C₆H₆), copper(I) triflate toluene complex (CuOTf.C₆H₅CH₃), copper(II) chloride (CuCl₂) (including dihydrate), copper(II) bromide (CuBr₂), copper (II) acetate (Cu(OAc)₂), copper(II) triflate (Cu(OTf)₂), copper(II) bis(trifluoromethanesulfonyl)imide (Cu(NTf₂)₂), silver chloride (AgCl), silver(I) triflate (AgOTf), zinc chloride (ZnCl₂), zinc bromide (ZnBr₂), zinc(II) triflate (Zn(OTf)₂), boron trifluoride ethyl ether complex (BF₃—OEt₂), boron trifluoride butyl ether complex (BF₃.n-Bu₂O), boron trifluoride tetrahydrofuran ether complex (BF₃.THF), aluminum chloride (AlCl₃), aluminum bromide (AlBr₃), tin(II) triflate (Sn(OTf)₂), and tin(IV) chloride (SnCl₄).

For e-1 and e-2 above, more preferred specific examples of Lewis acid include the following: magnesium triflate (Mg(OTf)₂), magnesium bis(trifluoromethanesulfonyl)imide (Mg(NTf₂)₂), calcium triflate (Ca(OTf)₂), calcium bis (trifluoromethanesulfonyl)imide (Ca(NTf₂)₂), scandium(III) triflate (Sc(OTf)₃), copper(II) chloride (CuCl₂) (including dihydrate), copper(II) bromide (CuBr₂), copper(II) acetate (Cu(OAc)₂), copper(II) triflate (Cu(OTf)₂), copper(II) bis (trifluoromethanesulfonyl)imide (Cu(NTf₂)₂), silver chloride (AgCl), and silver(I) triflate (AgOTf).

For e-1 and e-2 above, more preferred specific examples of Lewis acid include the following: calcium triflate (Ca(OTf)₂), copper(II) triflate (Cu(OTf)₂), and silver(I) triflate (AgOTf).

The transition metal triflate will be described. In one embodiment, the compound is formed from a transition metal ion as a cation and a triflate ion as an anion. The transition metal ion is as described above. The triflate ion is trifluoromethanesulfonic acid ion (CF₃SO₃⁻; TfO⁻) as described above.

The transition metal triflate formed from the transition metal ion and the triflate ion may include components other than the transition metal ion and the triflate ion.

In another embodiment, the transition metal triflate is a compound of the following formula:

M'Z'm wherein, M' is a transition metal ion as a cation,
Z is a triflate ion as an anion, and
m is an integer of 1 to 4,
wherein the transition metal ion is as described above, and the triflate ion is as described above.

Specific examples of the transition metal triflate are suitable examples among the specific examples of the above-described Lewis acid. Preferable specific examples of the transition metal triflate are suitable examples among the preferable specific examples of the above-described Lewis acid. More preferable specific examples of the transition metal triflate are suitable examples among the more preferable specific examples of the above-described Lewis acid. Even more preferable specific examples of the transition metal triflate are suitable examples among the even more preferable specific examples of the above-described Lewis acid.

e-3) In yet another embodiment, examples of the Lewis acid include halogens such as iodine, bromine, and chlorine. A more preferable specific example of the halogens is iodine.

f) Solid Acids

As the acid catalyst in the step (B), a solid acid can be used.

Examples of the solid acid include, but are not limited to, cation exchange resins, heteropoly acids, zeolites, montmorillonite, and alumina.

Herein, the term "cation exchange resin" is not particularly limited and means a known strongly acidic or weakly acidic cation exchange resin. Examples of the cation exchange resin include, but are not limited to, the DIAION (registered trademark) series (e.g., DIAION SK1B, SK110, SK116, P206, and WK40) manufactured by Mitsubishi Chemical Corporation, the AMBERLITE (registered trademark) series (e.g., AMBERLITE IR-120B, IR-200CT, IRC50, and IR-124) manufactured by Rohm and Haas Company, and the DOWEX (registered trademark) series (e.g., 50W-X8) manufactured by The Dow Chemical Company.

Examples of the heteropoly acids include, but are not limited to, 12-molybdo(VI)phosphoric acid n-hydrate (H₃[PMo₁₂O₄₀].nH₂O (n≈30)), 12-tungsto(VI)phosphoric acid n-hydrate (H₃[PW₁₂O₄₀].nH₂O (n≈30)), and 12-tungsto(VI) silicic acid n-hydrate (H₄[SiW₁₂O₄₀].nH₂O (n≈30, e.g., n≈26)). 12-Molybdo(VI)phosphoric acid n-hydrate is also referred to as phosphomolybdic acid n-hydrate. 12-Tungsto(VI)phosphoric acid n-hydrate is also referred to as phosphotungstic acid n-hydrate. 12-Tungsto(VI)silicic acid n-hydrate is also referred to as silicotungstic acid n-hydrate.

As the acid catalyst in the step (B), a salt of heteropoly acid can also be used.

Examples of the salt of the heteropoly acid include, but are not limited to, sodium 12-molybdo(VI)phosphate n-hydrate(Na₃[PMo₁₂O₄₀].nH₂O (n=30)). Sodium 12-molybdo(VI)phosphate n-hydrate is also referred to as sodium phosphomolybdate n-hydrate.

Examples of the zeolite include, but are not limited to, ZSM-5 type, mordenite type, L type, Y type, X type, and beta type.

Among the above-mentioned examples, preferable groups are as follows, but are not limited thereto.

One or more (preferably one to three, more preferably one or two, and even more preferably one) acid catalyst(s) selected from the group consisting of mineral acids, carboxylic acids, sulfonic acids, phosphoric acids, and Lewis acids are preferable.

One or more (preferably one to three, more preferably one or two, and even more preferably one) acid catalyst(s) selected from the group consisting of hydrochloric acid, sulfuric acid, nitric acid, trifluoroacetic acid, trichloroacetic acid, dichloroacetic acid, maleic acid, maleic anhydride, methanesulfonic acid, trifluoromethanesulfonic acid, benzenesulfonic acid, p-toluenesulfonic acid, 10-camphorsulfonic acid, phosphoric acid, ethyl phosphate, phenyl phosphate, diethyl phosphate, diphenyl phosphate, transition metal triflate, and iodine are more preferable.

One or more (preferably one to three, more preferably one or two, and even more preferably one) acid catalyst(s) selected from the group consisting of hydrochloric acid, sulfuric acid, nitric acid, trifluoroacetic acid, trichloroacetic acid, dichloroacetic acid, maleic acid, maleic anhydride, methanesulfonic acid, trifluoromethanesulfonic acid, benzenesulfonic acid, p-toluenesulfonic acid, 10-camphorsulfonic acid, diphenyl phosphate, copper(II) triflate, silver(I) triflate, and iodine are even more preferable.

One or more (preferably one to three, more preferably one or two, and even more preferably one) acid catalyst(s) selected from the group consisting of nitric acid, trifluoroacetic acid, trichloroacetic acid, dichloroacetic acid, maleic acid, maleic anhydride, methanesulfonic acid, trifluoromethanesulfonic acid, benzenesulfonic acid, p-toluenesulfonic acid, 10-camphorsulfonic acid, and diphenyl phosphate are even more preferable.

One or more (preferably one to three, more preferably one or two, and even more preferably one) acid catalyst(s) selected from the group consisting of nitric acid, trifluoroacetic acid, trichloroacetic acid, dichloroacetic acid, maleic acid, maleic anhydride, methanesulfonic acid, benzenesulfonic acid, p-toluenesulfonic acid, and diphenyl phosphate are still even more preferable.

One or more (preferably one to three, more preferably one or two, and even more preferably one) acid catalyst(s) selected from the group consisting of nitric acid, trifluoroacetic acid, trichloroacetic acid, maleic acid, maleic anhydride, benzenesulfonic acid, p-toluenesulfonic acid, and diphenyl phosphate are further preferable.

One or more (preferably one to three, more preferably one or two, and even more preferably one) acid catalyst(s) selected from the group consisting of nitric acid, trifluoroacetic acid, trichloroacetic acid, maleic acid, maleic anhydride, benzenesulfonic acid, and p-toluenesulfonic acid are further preferable.

One or more (preferably one to three, more preferably one or two, and even more preferably one) acid catalyst(s) selected from the group consisting of nitric acid, trifluoroacetic acid, trichloroacetic acid, maleic acid, maleic anhydride, and p-toluenesulfonic acid are further preferable.

One or more (preferably one to three, more preferably one or two, and even more preferably one) acid catalyst(s) selected from the group consisting of nitric acid, trifluoroacetic acid, maleic acid, and p-toluenesulfonic acid are further preferable.

Trifluoroacetic acid, maleic acid, or maleic anhydride is further preferable.

Trifluoroacetic acid or maleic acid is further preferable.

The acid catalyst in the step (B) may be used either alone or in combination of two or more kinds in any ratio. The form of the acid catalyst in the step (B) may be any form as long as the reaction proceeds. Examples of the form include a solid of only the acid catalyst, a liquid of only the acid catalyst, and a gas of only the acid catalyst, an aqueous solution with any concentration, and a solution in a solvent other than water (e.g., an organic solvent) with any concentration. The form can be appropriately selected by those skilled in the art.

The amount of the acid catalyst used in the step (B) may be any amount as long as the reaction proceeds. From the viewpoint of yield, suppression of by-product formation, and economic efficiency, the amount may be, for example, in the range of 0.001 to 1.0 mol, preferably 0.001 to 0.5 mol, more preferably 0.01 to 0.5 mol, even more preferably 0.01 to 0.3 mol, still even more preferably 0.01 to 0.2 mol, and further preferably 0.02 to 0.2 mol based on 1 mol of the compound of the formula (2).

(Base Catalyst in Step (B))

In the reaction of the step (B), the presence of an acid catalyst is essential, and the reaction may be performed in the presence of a base catalyst in addition to the acid catalyst. The base catalyst in the step (B) may be any base catalyst as long as the reaction proceeds. In addition, as long as the reaction proceeds, any of the following forms may be used and are included within the scope of the present invention. A free base can be used as the base catalyst. The base catalyst may be used in the form of a salt. When the base catalyst is a salt, the base catalyst may be either a simple salt or a double salt.

Examples of the base catalyst in the step (B) include the following, but are not limited thereto.

As the base catalyst, an amine is preferable.

The amine may be a primary amine, secondary amine, tertiary amine, or heterocyclic amine having the following formula:

wherein $R^3$, $R^4$ and $R^5$ are each independently hydrogen, an optionally substituted (C1-C6)alkyl; an optionally substituted (C3-C6)cycloalkyl, an optionally substituted (C2-C6)alkenyl; an optionally substituted (C2-C6)alkynyl; or an optionally substituted aryl; or any two of $R^3$, $R^4$ and $R^5$, together with the nitrogen atom to which they are attached, form a 4- to 12-membered heterocyclic ring, wherein the formed ring is optionally substituted; provided that at least one of $R^3$, $R^4$ and $R^5$ is not hydrogen.

Specific examples of the primary amine include, but are not limited to, methylamine, ethylamine, propylamine, butylamine, and aniline.

Specific examples of the secondary amine include, but are not limited to, diethylamine, dipropylamine, diisopropylamine, N-methylaniline (PhNHMe), N-ethylaniline, piperidine, and morpholine.

Specific examples of the tertiary amine include, but are not limited to, triethylamine, tripropylamine, tributylamine, diisopropylethylamine, 1,4-diazabicyclo[2.2.2]octane (DABCO), N,N-dimethylaniline, and N,N-diethylaniline.

Specific examples of the heterocyclic amine include, but are not limited thereto, pyridine, 4-(dimethylamino)-pyridine, 4-pyrrolidinopyridine, 2,6-lutidine, quinoline, isoquinoline, 1,8-diazabicyclo[5.4.0]-7-undec-7-ene (DBU), and 1,5-diazabicyclo[4.3.0]non-5-ene (DBN).

4-(Dimethylamino)-pyridine, 4-pyrrolidinopyridine, 1,8-diazabicyclo[5.4.0]-7-undec-7-ene (DBU), and 1,5-diazabicyclo[4.3.0]non-5-ene (DBN) also belong to the tertiary amine.

Examples of the amine also include imidazolinones. Specific examples of the imidazolinones include optical isomers such as (2S,5S)-2-tert-butyl-3-methyl-5-benzyl-4-imidazolinone and its diastereomers, and analogs thereof. However, since imidazolinones are expensive, it is industrially preferable not to use imidazolinones.

From the viewpoints of yield, economic efficiency, etc., preferable specific examples of the base catalyst include N-methylaniline, morpholine, and pyrrolidine, and more preferably include N-methylaniline.

The amount of the base catalyst used in the step (B) may be any amount as long as the reaction proceeds. However, it is preferred that the equivalent amount of the base catalyst be less than the equivalent amount of the acid catalyst. From the viewpoints of yield, suppression of by-products, economic efficiency, etc., the amount may be, for example, in the range of 0 (zero) to 1 equivalent, preferably 0 to 0.9 equivalents, more preferably 0 to 0.5 equivalents, and even more preferably 0 to 0.4 equivalents based on 1 equivalent of the acid catalyst. The range of 0.05 to 1 equivalent, preferably 0.05 to 0.9 equivalents, more preferably 0.1 to 0.5 equivalents, even more preferably 0.1 to 0.4 equivalents, and still even more preferably 0.2 to 0.4 equivalents based on 1 equivalent of the acid catalyst can also be mentioned as examples.

(Solvent in Step (B))

The reaction of the step (B) may be performed in the presence or absence of a solvent. Whether a solvent is used in the step (B) or not can be appropriately determined by a person skilled in the art. The solvent in the step (B) may be any solvent as long as the reaction in the step (B) proceeds. The solvent can be selected appropriately by a person skilled in the art.

Examples of the solvent in the step (B) include, but are not limited to, water, alcohols (e.g., methanol, ethanol, 2-propanol, butanol, and tert-butanol (tert-butanol is also referred to as tert-butyl alcohol)), ethers (e.g., tetrahydrofuran (THF), 1,4-dioxane, diisopropyl ether, dibutyl ether, di-tert-butyl ether, cyclopentyl methyl ether (CPME), methyl tert-butyl ether, 1,2-dimethoxyethane (DME), diglyme, and triglyme), nitriles (e.g., acetonitrile), amides (e.g., N,N-dimethylformamide (DMF), N,N-dimethylacetamide (DMAC), and N-methylpyrrolidone (NMP)), alkyl ureas (e.g., N,N'-dimethylimidazolidinone (DMI)), sulfoxides (e.g., dimethyl sulfoxide (DMSO)), sulfones (e.g., sulfolane), carboxylic acid esters (e.g., ethyl acetate and butyl acetate), aromatic hydrocarbon derivatives (e.g., benzene, toluene, xylenes, chlorobenzene, dichlorobenzenes, and nitrobenzene), aliphatic hydrocarbons (e.g., hexane, heptane, octane, cyclohexane, and ethylcyclohexane), and halogenated aliphatic hydrocarbons (e.g., dichloromethane, chloroform, and 1,2-dichloroethane (EDC)), and any combination thereof in any ratio.

From the viewpoints of reactivity, yield, economic efficiency, etc., in one embodiment, preferable examples of the solvent in the step (B) include water, alcohols, nitriles, ethers, aromatic hydrocarbon derivatives, halogenated aliphatic hydrocarbons, and any combination thereof in any ratio, more preferably water, nitriles, aromatic hydrocarbon derivatives, halogenated aliphatic hydrocarbons, and any combination thereof in any ratio, even more preferably water, aromatic hydrocarbon derivatives, halogenated aliphatic hydrocarbons, and any combination thereof in any ratio, still even more preferably water, halogenated aliphatic hydrocarbons, and any combination thereof in any ratio, and further preferably any combination of water and a halogenated aliphatic hydrocarbon in any ratio. Preferable specific examples of the solvent in the step (B) include water, methanol, ethanol, 2-propanol, tert-butanol, acetonitrile, tetrahydrofuran (THF), toluene, xylene, chlorobenzene, dichlorobenzene, dichloromethane, and any combination thereof in any ratio, more preferably water, acetonitrile, toluene, xylene, chlorobenzene, dichlorobenzene, dichloromethane, and any combination thereof in any ratio, even more preferably water, toluene, xylene, chlorobenzene, dichlorobenzene, dichloromethane, and any combination thereof in any ratio, still even more preferably water, dichloromethane, and any combination thereof in any ratio, and further preferably any combination of water and dichloromethane in any ratio. In any case, water is present. In another embodiment, preferable examples of the solvent in the step (B) include water, alcohols, nitriles, ethers, aromatic hydrocarbon derivatives, halogenated aliphatic hydrocarbons, and any combination thereof in any ratio, more preferably water, alcohols, nitriles, halogenated aliphatic hydrocarbons, and any combination thereof in any ratio, even more preferably water, nitriles, halogenated aliphatic hydrocarbons, and any combination thereof in any ratio, still even more preferably water, halogenated aliphatic hydrocarbons, and any combination thereof in any ratio, and further preferably any combination of water and a halogenated aliphatic hydrocarbon in any ratio. Preferable specific examples of the solvent in the step (B) include water, methanol, ethanol, 2-propanol, tert-butanol, acetonitrile, tetrahydrofuran (THF), toluene, xylene, chlorobenzene, dichlorobenzene, dichloromethane, and any combination thereof in any ratio, more preferably water, methanol, ethanol, 2-propanol, tert-butanol, acetonitrile, dichloromethane, and any combination thereof in any ratio, even more preferably water, acetonitrile, dichloromethane, and any combination thereof in any ratio, still even more preferably water, dichloromethane, and any combination thereof in any ratio, and further preferably any combination of water and dichloromethane in any ratio. In any case, water is present. In still another embodiment, preferable examples of the solvent in the step (B) include alcohols, nitriles, ethers, aromatic hydrocarbon derivatives, halogenated aliphatic hydrocarbons, and any combination thereof in any ratio, more preferably nitriles, aromatic hydrocarbon derivatives, halogenated aliphatic hydrocarbons, and any combination thereof in any ratio, even more preferably aromatic hydrocarbon derivatives, halogenated aliphatic hydrocarbons, and any combination thereof in any ratio, and particularly preferably halogenated aliphatic hydrocarbons. Preferable specific examples of the solvent in the step (B) include methanol, ethanol, 2-propanol, tert-butanol, acetonitrile, tetrahydrofuran (THF), toluene, xylene, chlorobenzene, dichlorobenzene, dichloromethane, and any combination thereof in any ratio, more preferably acetonitrile, toluene, xylene, chlorobenzene, dichlorobenzene, dichloromethane, and any combination thereof in any ratio, even more preferably toluene, xylene, chlorobenzene, dichlorobenzene, dichloromethane, and any combination thereof in any ratio, and particularly preferably dichloromethane. In still another embodiment, preferable examples of the solvent in the step (B) include alcohols, nitriles, ethers, aromatic hydrocarbon derivatives, halogenated aliphatic hydrocarbons, and any combination thereof in any ratio, more preferably alcohols, nitriles, halogenated aliphatic hydrocarbons, and any combination thereof in any ratio, even more preferably nitriles, halogenated aliphatic hydrocarbons, and any combination thereof in any ratio, and particularly preferably halogenated aliphatic hydrocarbons. Preferable specific examples of the solvent in the step (B) include methanol, ethanol, 2-propanol, tert-butanol, acetonitrile, tetrahydrofuran (THF), toluene, xylene, chlorobenzene, dichlorobenzene, dichloromethane, and any combination thereof in any ratio, more preferably methanol, ethanol, 2-propanol, tert-butanol, acetonitrile, dichloromethane, and any combination thereof in any ratio, even more preferably acetonitrile, dichloromethane, and any combination thereof in any ratio, and particularly preferably dichloromethane.

The amount of the solvent used in the step (B) may be any amount as long as the reaction system can be sufficiently stirred. From the viewpoints of yield, suppression of by-products, economic efficiency, etc., the amount may be, for example, in the range of 0 (zero) to 10 L (liters), preferably 0 to 5 L, more preferably 0.05 to 2 L, even more preferably 0.1 to 2 L, and further preferably 0.1 to 1 L based on 1 mol of the compound of the formula (2). However, the amount can be adjusted appropriately by a person skilled in the art. When a combination of two or more solvents is used, the ratio of the two or more solvents may be any ratio as long as the reaction proceeds. The ratio can be adjusted appropriately by a person skilled in the art. The solvent may be in a single layer or may be separated into two layers as long as the reaction proceeds.

(Reaction Temperature in Step (B))

The reaction temperature in the step (B) is not particularly limited. From the viewpoints of yield, suppression of by-products, economic efficiency, etc., the reaction temperature may be, for example, in the range of −10° C. (minus 10° C.) to 160° C., preferably 0° C. to 100° C., more preferably 10° C. to 100° C., still more preferably 10° C. to 80° C., and further preferably 10° C. to 50° C. However, the reaction temperature can be adjusted appropriately by a person skilled in the art.

(Reaction Time in Step (B))

The reaction time in the step (B) is not particularly limited. From the viewpoints of yield, suppression of by-products, economic efficiency, etc., the reaction time may be, for example, in the range of 0.5 hours to 72 hours, preferably 1 hour to 48 hours, more preferably 1 hour to 24 hours, and even more preferably 2 hours to 24 hours. However, the reaction time can be adjusted appropriately by a person skilled in the art.

(Product in Step (B): Compound of Formula (3))

The product in the step (B) is a 5,5-disubstituted-4,5-dihydroisoxazole corresponding to the compound of the formula (2) used as a raw material. Specific examples of the compound of the formula (3) to be obtained in the step (B) include the following, but are not limited thereto; 5,5-dimethyl-4,5-dihydroisoxazole, 5-ethyl-5-methyl-4,5-dihydroisoxazole, 5,5-diethyl-4,5-dihydroisoxazole, 5-isopropyl-5-methyl-4,5-dihydroisoxazole, 5-(tert-butyl)-5-methyl-4,5-dihydroisoxazole, 5-(chloromethyl)-5-methyl-4,5-dihydroisoxazole, 5-methyl-5-(trifluoromethyl)-4,5-dihydroisoxazole, 5-cyclopropyl-5-methyl-4,5-dihydroisoxazole, 5-oxa-6-azaspiro[3.4]oct-6-ene, 1-methyl-2-methyl[4.4]non-2-ene, 1-methyl-2-methyl[4.5]dec-2-ene, 5-butyl-5-methyl-4,5-dihydroisoxazole, 5-methyl-5-(4-methylpent-3-en-1-yl)-4,5-dihydroisoxazole, 5-methyl-5-(4-methylpentyl)-4,5-dihydroisoxazole, 4'H-spiro[fluorene-9,5'-isoxazole], 5,5-diphenyl-4,5-dihydroisoxazole, 5,5-bis(4-methylphenyl)-4,5-dihydroisoxazole, 5,5-bis(4-methoxyphenyl)-4,5-dihydroisoxazole, 5,5-bis(4-chlorophenyl)-4,5-dihydroisoxazole, 5-methyl-5-phenyl-4,5-dihydroisoxazole, 5-ethyl-5-phenyl-4,5-dihydroisoxazole, 5-(4-methylphenyl)-5-methyl-4,5-dihydroisoxazole, 5-(4-methoxyphenyl)-5-methyl-4,5-dihydroisoxazole, and 5-(4-chlorophenyl)-5-methyl-4,5-dihydroisoxazole. From the viewpoints of the usefulness of the product, etc., preferable specific examples of the compound of the formula (3) is 5,5-dimethyl-4,5-dihydroisoxazole.

Unless otherwise indicated, it is understood that numbers used herein to express characteristics such as quantities, sizes, concentrations, and reaction conditions are modified by the term "about". In some embodiments, disclosed numerical values are interpreted applying the reported number of significant digits and conventional rounding techniques. In some embodiments, disclosed numerical values are interpreted as containing certain errors necessarily resulting from the standard deviation found in their respective testing measurements.

Hereinafter, the present invention will be described in more detail by Examples, but the present invention is not limited in any way by these Examples.

Herein, room temperature is 10° C. to 35° C.

Example 1

Production of 3-methyl-2-butenal oxime (2-a)

Step (A; Oximation)

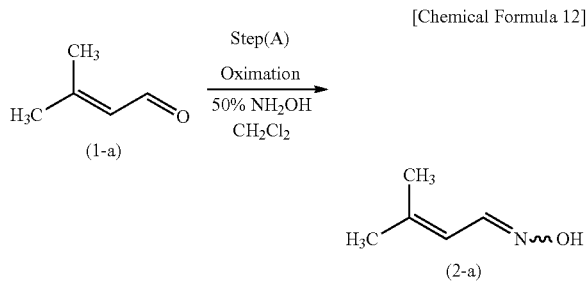

3-Methyl-2-butenal (1-a, 10.0 g, 119 mmol, 100 mol %) was dissolved in dichloromethane (60 ml, 0.5 L/mol). A 50% hydroxylamine aqueous solution (7.9 g, 119 mmol, 100 mol %) was added dropwise thereto such that the internal temperature became 30 to 40° C. (exothermic reaction). After the completion of the dropwise addition, the mixture was stirred at room temperature for 4 hours. After the completion of the reaction, a sodium chloride aqueous solution (10 ml) was added, followed by stirring. The resultant mixture was partitioned between an organic layer and an aqueous layer. The organic layer and the aqueous layer were separated from each other, so that the organic layer was obtained. The obtained organic layer was dried over magnesium sulfate, and concentrated under reduced pressure to obtain 3-methyl-2-butenal oxime (2-a, colorless semisolid, 11.9 g, purity: 98% (GC area percentage), 118 mmol, yield: 99% (quantitative), E/Z ratio: 61/39 (GC area percentage)).

$^1$H-NMR (400 MHz, CDCl$_3$) δ (ppm, relative to TMS): 1.82-1.84 (m, 3H, E isomer), 1.85-1.87 (m, 3H, E isomer), 1.87-1.89 (m, 3H, Z isomer), 1.90-1.92 (m, 3H, Z isomer), 5.91 (dq, J=1.3, 10.4 Hz, 1H, E isomer), 6.52 (dq, J=1.3, 9.9 Hz, 1H, Z isomer), 7.34 (d, J=9.9 Hz, 1H, Z isomer), 8.04 (d, J=10.4 Hz, 1H, E isomer), 8.40 (bs, 1H, E and/or Z isomer).

$^{13}$C-NMR (100 MHz, CDCl$_3$) δ (ppm): 18.5 (E and Z isomers), 26.1 (Z isomer), 26.4 (E isomer), 113.5 (Z isomer), 118.1 (E isomer), 144.1 (E isomer), 145.1 (Z isomer), 146.5 (Z isomer), 148.7 (E isomer).

Example 2

Production of 5,5-dimethyl-4,5-dihydroisoxazole (3-a)

Step (B; Cyclization)

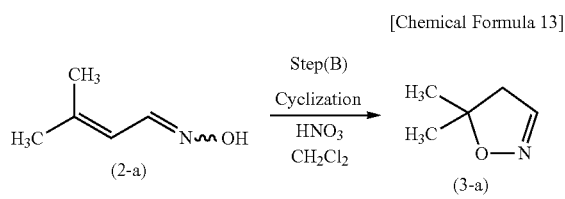

[Chemical Formula 13]

3-Methyl-2-butenal oxime (2-a, 11.9 g, purity: 98% (GC area percentage), 118 mmol, 100 mol %, E/Z ratio: 61/39 (GC area percentage)) prepared in the same manner as Example 1 was dissolved in dichloromethane (24 ml, 0.2 L/mol). Then, 69% nitric acid (1.1 g, 11.8 mmol, 10 mol %) was added thereto, followed by stirring at room temperature for 48 hours. The GC analysis (area percentage) of the reaction mixture revealed that the main components in the reaction mixture excluding the solvents and the like were as follows; 5,5-dimethyl-4,5-dihydroisoxazole (3-a; target product): 95%, 3-methyl-2-butenal oxime (2-a; raw material): 3%. Diethyl ether (30 ml) was added to the reaction mixture, and the resultant mixture was partitioned between an organic layer and an aqueous layer. The organic layer and the aqueous layer were separated from each other, so that the organic layer was obtained. The organic layer was washed successively with a sodium carbonate aqueous solution and a sodium chloride aqueous solution, dried over magnesium sulfate, and concentrated under reduced pressure. The resultant crude product was purified by distillation under reduced pressure to obtain 5,5-dimethyl-4,5-dihydroisoxazole (3-a; colorless oil, 8.4 g, purity: 99% (GC area percentage), 85.6 mmol, yield: 73%, boiling point: 75 to 77° C./50 Torr).

$^1$H-NMR (400 MHz, CDCl$_3$) δ (ppm, relative to TMS): 1.40 (s, 6H), 2.75 (d, J=1.9 Hz, 2H), 7.06 (s, 1H).

Boiling point: 154.9° C./1 atm (TG-DTA: thermogravimetric analysis-Differential thermal analysis). The following instrument was used for TG-DTA; Instrument: DSC 3100 S (manufactured by MAC Science Co., Ltd.).

Example 3

Production of 5,5-dimethyl-4,5-dihydroisoxazole (3-a)

Step (A; Oximation) and Step (B; Cyclization)

(1) Oximation

3-Methyl-2-butenal (1-a, 15.0 g, 178 mmol, 100 mol %) was dissolved in dichloromethane (90 ml, 0.5 L/mol). A 50% hydroxylamine aqueous solution (11.8 g, 178 mmol, 100 mol %) was added dropwise thereto such that the internal temperature became 30 to 40° C. (exothermic reaction). After the completion of the dropwise addition, the mixture was stirred at room temperature for 4 hours. After the completion of the reaction, a sodium chloride aqueous solution (10 ml) was added, followed by stirring. The resultant mixture was partitioned between an organic layer and an aqueous layer. The organic layer and the aqueous layer were separated from each other, so that the organic layer was obtained. The resultant organic layer was dried over magnesium sulfate, and concentrated under reduced pressure (400 Torr) at 40° C. (bath temperature) until the amount of the organic layer became 36 g to obtain crude 3-methyl-2-butenal oxime (yield: quantitative, containing about 14 ml of dichloromethane).

(2) Cyclization Reaction

To the mixture of 3-methyl-2-butenal oxime and dichloromethane obtained in (1) above, dichloromethane (22 ml) was added such that the total amount of dichloromethane in the reaction system became approximately 36 ml (0.2 L/mol). Trifluoroacetic acid (TFA, 2.03 g, specific gravity: 1.49, 1.36 ml, 17.8 mmol, 10 mol %) was added thereto, followed by stirring at room temperature for 48 hours. The GC analysis (area percentage) of the reaction mixture revealed that the main components in the reaction mixture excluding the solvents and the like were as follows; 5,5-dimethyl-4,5-dihydroisoxazole (3-a; target product): 94%, 3-methyl-2-butenal oxime (2-a; intermediate): 1%. Diethyl ether (40 ml) was added to the reaction mixture, and the resultant mixture was partitioned into an organic layer and an aqueous layer. The organic layer and the aqueous layer were separated from each other, so that the organic layer was obtained. The organic layer was washed successively with a sodium carbonate aqueous solution and a sodium chloride aqueous solution, dried over magnesium sulfate, and concentrated under reduced pressure. The resultant crude product was purified by distillation under reduced pressure to obtain 5,5-dimethyl-4,5-dihydroisoxazole (3-a, colorless oil, 13.7 g, purity: 99% (GC area percentage), 137 mmol, yield: 77% (2 steps), boiling point: 75 to 77° C./50 Torr).

Example 4

Production of 5,5-dimethyl-4,5-dihydroisoxazole (3-a)

Step (A; Oximation) and Step (B; Cyclization)

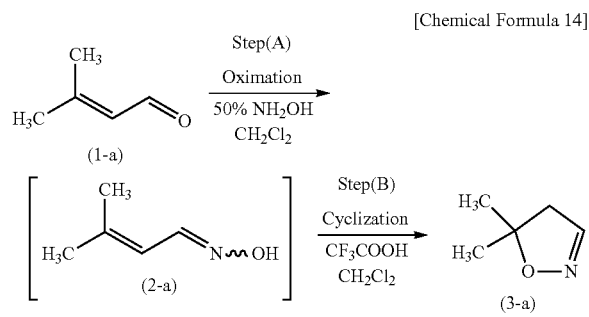

[Chemical Formula 14]

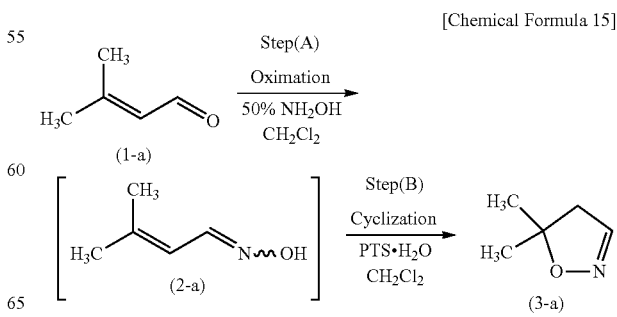

[Chemical Formula 15]

(1) Oximation

3-Methyl-2-butenal (1-a, 10.0 g, 119 mmol, 100 mol %) was dissolved in dichloromethane (60 ml, 0.5 L/mol). A 50% hydroxylamine aqueous solution (7.9 g, 119 mmol, 100 mol %) was added dropwise thereto such that the internal temperature became 30 to 40° C. (exothermic reaction). After the completion of the dropwise addition, the mixture was stirred at room temperature for 4 hours. After the completion of the reaction, a sodium chloride aqueous solution (10 ml) was added, followed by stirring. The resultant mixture was partitioned between an organic layer and an aqueous layer. The organic layer and the aqueous layer were separated from each other, so that the organic layer was obtained. The resultant organic layer was dried over magnesium sulfate, and concentrated under reduced pressure (400 Torr) at 40° C. (bath temperature) until the amount of the organic layer became 31 g to obtain crude 3-methyl-2-butenal oxime (yield: quantitative, containing about 14 ml of dichloromethane).

(2) Cyclization Reaction

To the mixture of 3-methyl-2-butenal oxime and dichloromethane obtained in (1) above, dichloromethane (10 ml) was added such that the total amount of dichloromethane in the reaction system became approximately 24 ml (0.2 L/mol). p-Toluenesulfonic acid monohydrate (PTS-H$_2$O, 2.3 g, 11.9 mmol, 10 mol %) was added thereto, followed by stirring at room temperature for 60 hours. The GC analysis (area percentage) of the reaction mixture revealed that the main components in the reaction mixture excluding the solvents and the like were as follows; 5,5-dimethyl-4,5-dihydroisoxazole (3-a; target product): 95%, 3-methyl-2-butenal oxime (2-a; intermediate): 3%. Diethyl ether (30 ml) was added to the reaction mixture, and the resultant mixture was partitioned between an organic layer and an aqueous layer. The organic layer and the aqueous layer were separated from each other, so that the organic layer was obtained. The organic layer was washed successively with a sodium carbonate aqueous solution and a sodium chloride aqueous solution, dried over magnesium sulfate, and concentrated under reduced pressure. The resultant crude product was purified by distillation under reduced pressure to obtain 5,5-dimethyl-4,5-dihydroisoxazole (3-a, colorless oil, 8.3 g, purity: 99% (GC area percentage), 83 mmol, yield: 70%, boiling point: 75 to 77° C./50 Torr).

Example 5

Production of 5,5-dimethyl-4,5-dihydroisoxazole (3-a)

Step (A; Oximation) and Step (B; Cyclization)

[Chemical Formula 16]

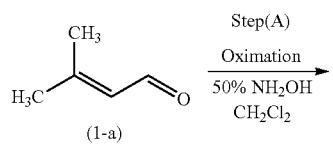

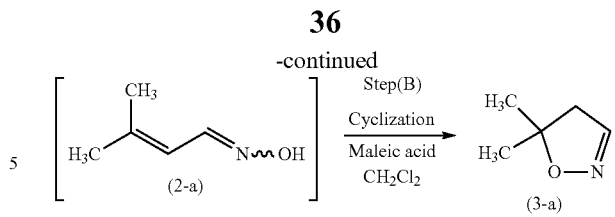

(1) Oximation

3-Methyl-2-butenal (1-a, 10.0 g, 119 mmol, 100 mol %) was dissolved in dichloromethane (60 ml, 0.5 L/mol). A 50% hydroxylamine aqueous solution (7.9 g, 119 mmol, 100 mol %) was added dropwise thereto such that the internal temperature became 30 to 40° C. (exothermic reaction). After the completion of the dropwise addition, the mixture was stirred at room temperature for 4 hours. After the completion of the reaction, a sodium chloride aqueous solution (10 ml) was added, followed by stirring. The resultant mixture was partitioned between an organic layer and an aqueous layer. The organic layer and the aqueous layer were separated from each other, so that the organic layer was obtained. The resultant organic layer was dried over magnesium sulfate, and concentrated under reduced pressure (400 Torr) at 40° C. (bath temperature) until the amount of the organic layer became 33 g to obtain crude 3-methyl-2-butenal oxime (yield: quantitative, containing about 16 ml of dichloromethane).

(2) Cyclization Reaction

To the mixture of 3-methyl-2-butenal oxime and dichloromethane obtained in (1) above, dichloromethane (8 ml) was added such that the total amount of dichloromethane in the reaction system became approximately 24 ml (0.2 L/mol). Then, maleic acid (1.38 g, 11.9 mmol, 10 mol %) was added thereto, followed by stirring at room temperature for 60 hours. The GC analysis (area percentage) of the reaction mixture revealed that the main components in the reaction mixture excluding the solvents and the like were as follows; 5,5-dimethyl-4,5-dihydroisoxazole (3-a; target product): 97%. 3-Methyl-2-butenal oxime (2-a; intermediate) had disappeared. Diethyl ether (30 ml) was added to the reaction mixture, and the resultant mixture was partitioned between an organic layer and an aqueous layer. The organic layer and the aqueous layer were separated from each other, so that the organic layer was obtained. The organic layer was washed successively with a sodium carbonate aqueous solution and a sodium chloride aqueous solution, dried over magnesium sulfate, and concentrated under reduced pressure. The resultant crude product was purified by distillation under reduced pressure to obtain 5,5-dimethyl-4,5-dihydroisoxazole (3-a, colorless oil, 9.3 g, purity: 99% (GC area percentage), 94 mmol, yield: 79%, boiling point: 75 to 77° C./50 Torr).

Example 6

Production of 5,5-dimethyl-4,5-dihydroisoxazole (3-a)

Step (B; Cyclization)

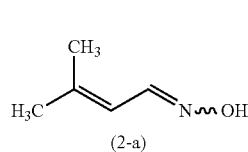
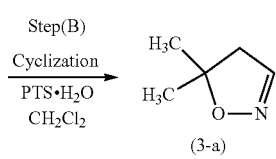

[Chemical Formula 17]

3-Methyl-2-butenal oxime (2-a; 215 mg, purity: 95% (quantitative NMR, internal standard: dimethylsulfone), 2.06 mmol, 100 mol %, E/Z ratio: 62/38 (NMR)) prepared in a similar manner to Example 1 was dissolved in dichloromethane (0.43 ml, 0.2 L/mol). p-Toluenesulfonic acid monohydrate (PTS·H$_2$O, 41 mg, 0.22 mmol, 10.5 mol %) was added thereto, followed by stirring at room temperature for 72 hours. The GC analysis (area percentage) of the reaction mixture revealed that the main components in the reaction mixture excluding the solvents and the like were as follows; 5,5-dimethyl-4,5-dihydroisoxazole (3-a; target product): 91%, 3-methyl-2-butenal oxime (2-a; raw material): 6%. Quantitative NMR analysis using dimethyl sulfone (62.4 mg, 0.663 mmol) as an internal standard revealed that the yield of 5,5-dimethyl-4,5-dihydroisoxazole (3-a; target product) was 74% (151 mg, 1.52 mmol).

Examples 7 to 29 and Comparative Example 1

Production of 5,5-dimethyl-4,5-dihydroisoxazole (3-a)

Step (B; Cyclization); Study on Cyclization Catalysts

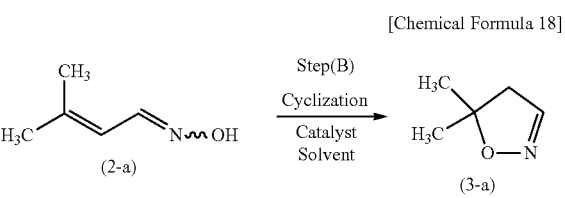

[Chemical Formula 18]

The above reaction was performed by using 3-methyl-2-butenal oxime (2-a) prepared in a similar manner to Example 1 as a raw material and changing the reaction conditions as shown in the table below.

That is, 3-methyl-2-butenal oxime (2-a, 100 mg, E/Z ratio: 62/38 (NMR)) as a raw material was dissolved in a solvent shown in the table below and a catalyst shown in the table below was added thereto, and the resultant mixture was stirred at a prescribed temperature for a prescribed time. In Example 9, 10 mol % of tetrabutylammonium hexafluorophosphate (Bu$_4$N$^+$PF$_6^-$) was added. In Example 12, 0.5 g of the raw material was used. The results are shown in the table below. In the table below, a result of GC analysis (area percentage) of a reaction mixture is shown as a yield.

TABLE 1

| Example | Cyclization Catalysts (mol %) | Solvent (L/mol) | | Temperature (° C) | Time (h) | Yield (%) Target Compound (3-a) | Raw Material (2-a) |
|---|---|---|---|---|---|---|---|
| Exmaple 7 | AgOTf 5 | EDC | 1 | 80 | 5 | 70 | 27 |
| Example 8 | Cu(OTf)$_2$ 5 | EDC | 1 | r.t. | 48 | 78 | 2 |
| Example 9 | Ca(NTf)$_2$ 5 | CH$_2$Cl$_2$ | 0.5 | r.t. | 24 | 71 | 14 |
| Example 10 | I$_2$ 5 | CH$_2$Cl$_2$ | 1 | 50 | 48 | 83 | 15 |
| Exmaple 11 | H$_2$SO$_4$ 10 | CH$_2$Cl$_2$ | 1 | r.t. | 15 | 71 | 17 |
| Example 12 | 35% HCl 10 | CH$_2$Cl$_2$ | 0.5 | r.t. | 20 | 86 | 15 |
| Example 13 | 69% HNO$_3$ 10 | CH$_2$Cl$_2$ | 0.5 | r.t. | 20 | 91 | 6 |
| Example 14 | 69% HNO$_3$ 10 | Toluene | 0.5 | r.t. | 20 | 71 | 20 |
| Example 15 | CSA 5 | CH$_2$Cl$_2$ | 1 | 50 | 10 | 83 | 14 |
| Example 16 | TsOH·H$_2$O 10 | CH$_2$Cl$_2$ | 1 | 50 | 5 | 81 | 15 |
| Example 17 | TsOH·H$_2$O 10 | CH$_2$Cl$_2$ | 0.5 | r.t. | 60 | 92 | 4 |
| Example 18 | TsOH·H$_2$O 10 | CH$_2$Cl$_2$ | 0.5 | r.t. | 24 | 79 | 17 |
| Example 19 | TsOH·H$_2$O 10 | CH$_2$Cl$_2$ | 0.2 | r.t. | 40 | 91 | 5 |
| Example 20 | TfOH 10 | CH$_2$Cl$_2$ | 0.5 | r.t. | 24 | 79 | 17 |
| Example 21 | MsOH 10 | CH$_2$Cl$_2$ | 0.5 | r.t. | 24 | 83 | 12 |
| Exmaple 22 | CF$_3$COOH 10 | CH$_2$Cl$_2$ | 0.5 | r.t. | 24 | 92 | 3 |
| Example 23 | CCl$_3$COOH 10 | CH$_2$Cl$_2$ | 0.5 | r.t. | 24 | 95 | 3 |
| Example 24 | CHCl$_2$COOH 10 | CH$_2$Cl$_2$ | 0.5 | r.t. | 24 | 79 | 15 |
| Example 25 | Maleic acid 10 | CH$_2$Cl$_2$ | 0.5 | r.t. | 24 | 93 | 3 |
| Example 26 | Maleic anhydride 10 | CH$_2$Cl$_2$ | 0.5 | r.t. | 24 | 95 | 0 |
| Example 27 | di-Ph Phosphate 10 | CH$_2$Cl$_2$ | 0.5 | r.t. | 24 | 85 | 11 |
| Example 28 | CF$_3$COOH· PhNHMe 10 | CH$_2$Cl$_2$ | 0.5 | r.t. | 24 | 46 | 25 |

TABLE 1-continued

| Example | Cyclization Catalysts (mol %) | Solvent (L/mol) | | Temperature (° C) | Time (h) | Yield (%) Target Compound (3-a) | Yield (%) Raw Material (2-a) |
|---|---|---|---|---|---|---|---|
| Example 29 | di-Ph Phosphate• PhNHMe | 10 CH$_2$Cl$_2$ | 0.5 | r.t. | 24 | 54 | 16 |
| Comparative Example 1 | PhNHMe | 10 CH$_2$Cl$_2$ | 0.5 | r.t. | 24 | 0 | 100 | r.t.: Room temperature
CH$_2$Cl$_2$: Dichloromethane
EDC: Ethylene dicloride (1, 2-dichloroethane)
AgOTf: Silver(I) triflate
Cu(OTf)$_2$: Cooper(II) triflate
Ca(NTf$_2$)$_2$: Calcium bis(trifluoromethanesulfonyl)imide
CAS: 10-Camphorsulfonic acid
TsOH•H$_2$O: p-Toluenesulfonic acid monohydrate
TfOH: Trifluoromethanesulfonic acid
MsOH: Methanesulfonic acid
di-Ph Phosphate: Diphenyl phosphate
PhNHMe: N-Methylaniline The results of Examples 7 to 27 show that various acid catalysts such as Lewis acids, mineral acids, sulfonic acids, carboxylic acids, and phosphoric acids are useful as a cyclization catalyst.

Examples 28 and 29 were performed under the same conditions as in Examples 22 and 27, except that the same equivalent amount of the base catalyst (N-methylaniline) as the equivalent amount of the acid catalyst was added. These examples show that, unexpectedly, the presence of the same equivalent amount of the base catalyst as the equivalent amount of the acid catalyst does not contribute to improvement in yield.

JP 2013-512202 A (Patent Document 2), Synlett 2008, No. 6, 827-830 (Non-Patent Document 1) and Chem. Eur. J. 2010, Vol. 16, 11325-11339 (Non-Patent Document 2) disclose processes of performing a cyclization reaction in the presence of an acid-base catalyst. In particular, Patent Document 2 discloses that it is preferable to perform the cyclization reaction in the presence of an acid-base catalyst containing an acid catalyst and the same equivalent amount of a base catalyst such as N-methylaniline as the equivalent amount of the acid catalyst, rather than in the presence of only an acid catalyst. However, in the process of the present invention, the presence of the same equivalent amount of the base catalyst as the equivalent amount of the acid catalyst did not improve the yield of the cyclization reaction. Therefore, when the present invention was compared with known technologies after the present invention was completed, it was suggested that the reaction mechanism of the cyclization reaction of the present invention was different from the reaction mechanism of Patent Document 2 and Non-Patent Documents 1 and 2. On the other hand, as shown in Example 32 below, even when both an acid catalyst and a base catalyst were used, the reaction proceeded in a high yield in the case where an excess amount of an acid catalyst over a base catalyst was used (in other words, in the case where a smaller amount of a base catalyst was used than an acid catalyst). Accordingly, the presence of a base catalyst is not excluded from the scope of the present invention. However, in any case, it is understood that the cyclization reaction of the present invention is different from those of Patent Document 2 and Non-Patent Documents 1 and 2.

Comparative Example 1 is an example in which a cyclization reaction was attempted without using an acid catalyst and with using only a base catalyst. The cyclization reaction did not proceed at all without using an acid catalyst and with using only a base catalyst.

Example 30

Production of 5,5-dimethyl-4,5-dihydroisoxazole (3-a)

Step (A; Oximation) and Step (B; Cyclization)

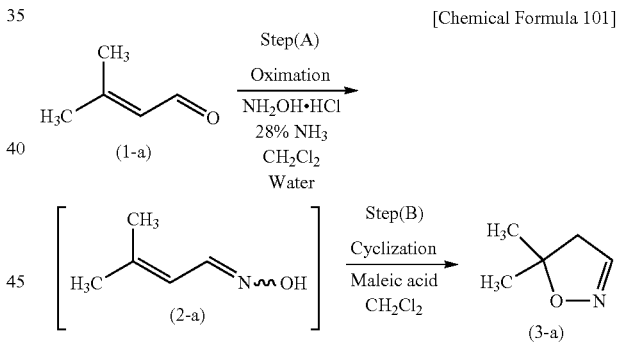

[Chemical Formula 101]

(1) Oximation

In a 25 ml round-bottom flask, water (12 ml) and dichloromethane (12 ml, 0.1 L/mol) were added to hydroxylamine hydrochloride (8.91 g, 128 mmol, 110 mol %), and then aqueous ammonia (7.80 g, purity: 28%, 128 mmol, 110 mol %) was added with stirring under ice cooling. 3-Methyl-2-butenal (10.0 g, purity 98% (GC area %), 117 mmol, 100 mol %) was added thereto such that the temperature did not exceed 30° C., followed by stirring at room temperature for 1 hour. The resultant mixture was partitioned between an organic layer and an aqueous layer. The organic layer and the aqueous layer were separated from each other. The aqueous layer was extracted with a small amount of dichloromethane. At this time, the pH of the aqueous layer was 6.6.

(2) Cyclization Reaction

In a 50 ml round-bottom flask, the organic layers obtained in the above (1) were combined (dichloromethane used: 23 ml in total, 0.2 L/mol in total). Maleic acid (1.35 g, 11.7 mmol, 10 mol %) was added thereto, followed by stirring at 30° C. for 48 hours. The GC analysis (area percentage) of the reaction mixture revealed that the components in the reaction mixture excluding the solvents and the like were as follows; 5,5-dimethyl-4,5-dihydroisoxazole (3-a; target product): 96%.

After the completion of the reaction, a saturated sodium hydrogen carbonate aqueous solution (12 ml) was added, followed by stirring. The resultant mixture was partitioned between an organic layer and an aqueous layer. The organic layer and the aqueous layer were separated from each other. The aqueous layer was extracted with a small amount of dichloromethane, and the combined organic layer was concentrated under reduced pressure. The resultant crude product was purified by distillation under reduced pressure to give 5,5-dimethyl-4,5-dihydroisoxazole (3-a, colorless oil, 9.5 g, yield: 82%, boiling point: 75 to 77° C./50 Torr).

Example 31

Production of 5,5-dimethyl-4,5-dihydroisoxazole (3-a)

Step (A; Oximation) and Step (B; Cyclization)

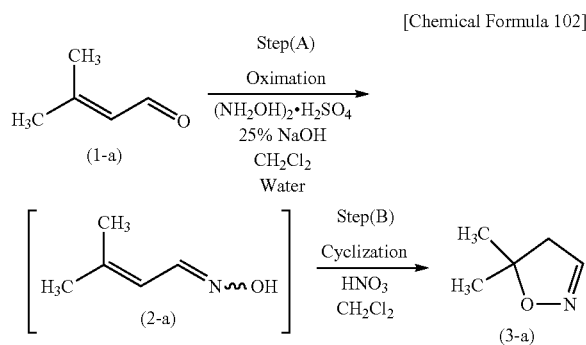

[Chemical Formula 102]

(1) Oximation

In a 25 ml round-bottom flask, water (5 ml) and dichloromethane (12 ml, 0.1 L/mol) were added to hydroxylamine sulfate (10.5 g, 128 mmol in terms of hydroxylamine ($NH_2OH$), 110 mol % in terms of hydroxylamine ($NH_2OH$)), and then a 25% sodium hydroxide aqueous solution (about 20 g, 128 mmol, 110 mol %) was added with stirring under ice cooling until the pH became 6.9. 3-Methyl-2-butenal (10.0 g, purity 98% (GC area %), 117 mmol, 100 mol %) was added thereto such that the temperature did not exceed 30° C., followed by stirring at room temperature for 1 hour. The resultant mixture was partitioned between an organic layer and an aqueous layer. The organic layer and the aqueous layer were separated from each other. The aqueous layer was extracted with a small amount of dichloromethane.

(2) Cyclization reaction

In a 50 ml round-bottom flask, the organic layers obtained in the above (1) were combined (dichloromethane used: 23 ml in total, 0.2 L/mol in total). 70% Nitric acid (1.05 g, 11.7 mmol, 10 mol %) was added thereto, followed by stirring at 30° C. for 48 hours. The GC analysis (area percentage) of the reaction mixture revealed that the components in the reaction mixture excluding the solvents and the like were as follows; 5,5-dimethyl-4,5-dihydroisoxazole (3-a; target product): 84%.

After the completion of the reaction, a saturated sodium hydrogen carbonate aqueous solution (12 ml) was added, followed by stirring. The resultant mixture was partitioned between an organic layer and an aqueous layer. The organic layer and the aqueous layer were separated from each other. The aqueous layer was extracted with a small amount of dichloromethane, and the combined organic layer was concentrated under reduced pressure. The resultant crude product was purified by distillation under reduced pressure to obtain 5,5-dimethyl-4,5-dihydroisoxazole (3-a, colorless oil, 9.2 g, yield: 80%, boiling point: 75 to 77° C./50 Torr).

Example 32

Production of 5,5-dimethyl-4,5-dihydroisoxazole (3-a)

Step (A; Oximation) and Step (B; Cyclization)

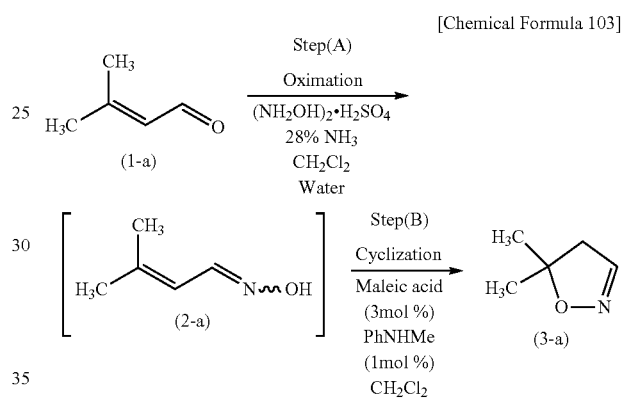

[Chemical Formula 103]

(1) Oximation

In a 25 ml round-bottom flask, water (12 ml) and dichloromethane (12 ml, 0.1 L/mol) were added to hydroxylamine sulfate (9.56 g, 117 mmol in terms of hydroxylamine ($NH_2OH$), 100 mol % in terms of hydroxylamine ($NH_2OH$)), and then aqueous ammonia (7.09 g, purity: 28%, 117 mmol, 100 mol %) was added with stirring under ice cooling. 3-Methyl-2-butenal (10.2 g, purity 98% (GC area %), 119 mmol, 102 mol %) was added thereto such that the temperature did not exceed 30° C., followed by stirring at room temperature for 1 hour. The resultant mixture was partitioned between an organic layer and an aqueous layer. The organic layer and the aqueous layer were separated from each other. The aqueous layer was extracted with a small amount of dichloromethane.

(2) Cyclization Reaction

In a 50 ml round-bottom flask, the organic layers obtained in the above (1) were combined (dichloromethane used: 23 ml in total, 0.2 L/mol in total). Maleic acid (406 mg, 3.50 mmol, 3 mol %) and N-methylaniline (126 μl, specific gravity: 0.99 (20° C.), 125 mg, 1.17 mmol, 1 mol %) were added thereto, followed by stirring at 30° C. for 48 hours. The GC analysis (area percentage) of the reaction mixture revealed that the components in the reaction mixture excluding the solvents and the like were as follows; 5,5-dimethyl-4,5-dihydroisoxazole (3-a; target product): 93%.

After the completion of the reaction, a saturated sodium hydrogen carbonate aqueous solution (12 ml) was added, followed by stirring. The resultant mixture was partitioned between an organic layer and an aqueous layer. The organic layer and the aqueous layer were separated from each other. The aqueous layer was extracted with a small amount of dichloromethane, and the combined organic layer was concentrated under reduced pressure. The resultant crude product was purified by distillation under reduced pressure to obtain 5,5-dimethyl-4,5-dihydroisoxazole (3-a, colorless oil, 8.9 g, yield: 75%, boiling point: 75 to 77° C./50 Torr).

INDUSTRIAL APPLICABILITY

The 5,5-disubstituted-4,5-dihydroisoxazole of the formula (3) produced by the process of the present invention is useful as an intermediate for producing pharmaceuticals and agricultural chemicals etc., particularly, a herbicide pyroxasulfone. According to the present invention, the generation of by-products and/or wastes can be suppressed, and atom efficiency can be improved. Furthermore, according to the present invention, the target compound can be efficiently produced by a simple operation even if an inexpensive catalyst is used. Therefore, the process of the present invention is industrially preferable, economical, and environmentally friendly, and has high industrial utility value. In short, the present invention has high industrial applicability.

The invention claimed is:
1. A process for producing a compound of the formula (3):

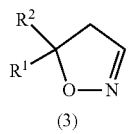

wherein $R^1$ and $R^2$ are each independently a (C1-C4) alkyl,
which comprises the following step:
step (B): reacting a compound of the formula (2) in the presence of an acid catalyst to produce the compound of the formula (3),

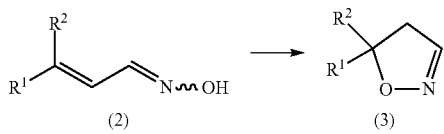

wherein $R^1$ and $R^2$ are as defined above.

2. The process according to claim 1, wherein the compound of the formula (2) is produced by a process comprising the following step (A),
step (A): reacting a compound of the formula (1) with an oximating agent to produce the compound of the formula (2),

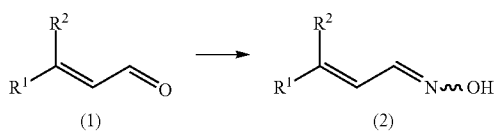

wherein, $R^1$ and $R^2$ are as defined above.

3. The process according to claim 2, wherein the oximating agent in the step (A) is hydroxylamine or a salt thereof.

4. The process according to claim 2, wherein the oximating agent in the step (A) is hydroxylamine, hydroxylamine hydrochloride or hydroxylamine sulfate.

5. The process according to claim 2, wherein the reaction of the step (A) is performed in the presence of a base.

6. The process according to claim 5, wherein the base in the step (A) is sodium hydroxide, potassium hydroxide, sodium carbonate, potassium carbonate, sodium hydrogen carbonate, potassium hydrogen carbonate or ammonia.

7. The process according to claim 2, wherein the reaction of the step (A) is performed in the presence of one or more solvents selected from water, acetonitrile, toluene, xylene, chlorobenzene, dichlorobenzene and dichloromethane.

8. The process according to claim 2, wherein the reaction of the step (A) is performed in the presence of a solvent composed of a combination of water and dichlorobenzene.

9. The process according to claim 1, wherein the acid catalyst in the step (B) is one or more acid catalysts selected from the group consisting of mineral acids, carboxylic acids, sulfonic acids, phosphoric acids and Lewis acids.

10. The process according to claim 1, wherein the acid catalyst in the step (B) is one or more acid catalysts selected from the group consisting of nitric acid, trifluoroacetic acid, trichloroacetic acid, maleic acid, maleic anhydride, benzenesulfonic acid and p-toluenesulfonic acid.

11. The process according to claim 1, wherein the acid catalyst in the step (B) is trifluoroacetic acid or maleic acid.

12. The process according to claim 1, wherein the reaction of the step (B) is performed in the presence of 0.1 to 0.5 equivalents of a base catalyst based on 1 equivalent of the acid catalyst.

13. The process according to claim 12, wherein the base catalyst in the step (B) is N-methylaniline, morpholine or pyrrolidine.

14. The process according to claim 1, wherein the reaction of the step (B) is performed in the presence of one or more solvents selected from water, acetonitrile, toluene, xylene, chlorobenzene, dichlorobenzene and dichloromethane.

15. The process according to claim 1, wherein the reaction of the step (B) is performed in the presence of dichlorobenzene solvent.

16. The process according to claim 1, wherein the compound of the formula (2) is 3-methyl-2-butenal oxime, and the compound of the formula (3) is 5,5-dimethyl-4,5-dihydroisoxazole.

17. The process according to claim 7, wherein the acid catalyst in the step (B) is one or more acid catalysts selected from the group consisting of nitric acid, trifluoroacetic acid, trichloroacetic acid, maleic acid, maleic anhydride, benzenesulfonic acid and p-toluenesulfonic acid.

18. The process according to claim 7, wherein the reaction of the step (B) is performed in the presence of one or more solvents selected from water, acetonitrile, toluene, xylene, chlorobenzene, dichlorobenzene and dichloromethane.

19. The process according to claim 7, wherein the compound of the formula (2) is 3-methyl-2-butenal oxime, and the compound of the formula (3) is 5,5-dimethyl-4,5-dihydroisoxazole.

20. The process according to claim 17, wherein the compound of the formula (2) is 3-methyl-2-butenal oxime, and the compound of the formula (3) is 5,5-dimethyl-4,5-dihydroisoxazole.

* * * * *